US012765893B2

(12) United States Patent
Korman et al.

(10) Patent No.: US 12,765,893 B2
(45) Date of Patent: Oct. 20, 2026

(54) TARGETING GUIDES

(71) Applicant: WRIGHT MEDICAL TECHNOLOGY, INC., Memphis, TN (US)

(72) Inventors: Zachary Korman, St. Louis, MO (US); Paul Luttrell, Germantown, TN (US); Joseph Ryan Woodard, Memphis, TN (US); Gary W. Lowery, Eads, TN (US); Peter George Mangone, Arden, NC (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 126 days.

(21) Appl. No.: 18/953,673

(22) Filed: Nov. 20, 2024

(65) Prior Publication Data

US 2025/0082346 A1 Mar. 13, 2025

Related U.S. Application Data

(63) Continuation of application No. 17/786,868, filed as application No. PCT/US2021/018293 on Feb. 17, 2021, now Pat. No. 12,185,958.

(60) Provisional application No. 62/984,043, filed on Mar. 2, 2020.

(51) Int. Cl.

| | |
|---|---|
| ***A61B 17/17*** | (2006.01) |
| ***A61B 17/72*** | (2006.01) |
| ***A61B 17/88*** | (2006.01) |

(52) U.S. Cl.

CPC .......... *A61B 17/1775* (2016.11); *A61B 17/17* (2013.01); *A61B 17/7291* (2013.01); *A61B 17/8897* (2013.01)

(58) Field of Classification Search

CPC .................................................. A61B 17/1775

See application file for complete search history.

(56) References Cited

U.S. PATENT DOCUMENTS

| | | | | |
|---|---|---|---|---|
| 8,343,199 | B2 | 1/2013 | Tyber et al. | |
| 8,506,606 | B2 | 8/2013 | Orbay et al. | |
| 2007/0173843 | A1* | 7/2007 | Matityahu | A61B 17/80 606/281 |
| 2007/0233112 | A1 | 10/2007 | Orbay et al. | |
| 2007/0239168 | A1* | 10/2007 | Kuenzi | A61B 17/1728 606/96 |
| 2009/0036931 | A1 | 2/2009 | Pech et al. | |
| 2012/0271314 | A1* | 10/2012 | Stemniski | A61B 17/1775 606/87 |
| 2014/0088594 | A1 | 3/2014 | Sasing | |

(Continued)

FOREIGN PATENT DOCUMENTS

| | | | |
|---|---|---|---|
| AU | 2013270545 | B2 | 7/2015 |
| FR | 3051349 | A1 | 11/2017 |

OTHER PUBLICATIONS

International Search Report and Written Opinion issued in connection with PCT/US2021/018293, Jun. 29, 2021, 18 pages.

(Continued)

*Primary Examiner* — Christian A Sevilla

(74) *Attorney, Agent, or Firm* — DUANE MORRIS LLP

(57) ABSTRACT

Disclosed are bone screw drill targeting guides and methods for using such targeting guides that are useful in surgical procedures for correcting hallux valgus deformity.

14 Claims, 32 Drawing Sheets

(56) References Cited

U.S. PATENT DOCUMENTS

| | | | | |
|---|---|---|---|---|
| 2014/0180348 | A1* | 6/2014 | Thoren | A61B 17/17<br>606/86 R |
| 2015/0305791 | A1 | 10/2015 | Purohit et al. | |
| 2015/0359580 | A1 | 12/2015 | Dacosta et al. | |
| 2017/0165073 | A1 | 6/2017 | Orbay et al. | |
| 2017/0196602 | A1 | 7/2017 | Lundquist et al. | |
| 2018/0168664 | A1* | 6/2018 | Dees | A61B 17/164 |
| 2018/0242987 | A1 | 8/2018 | Lintula et al. | |
| 2018/0242988 | A1 | 8/2018 | Dacosta et al. | |

OTHER PUBLICATIONS

Extended European Search Report issued in connection with corresponding European Patent Application No. 21765525.7, Nov. 16, 2023, 7 pages.

* cited by examiner

First configuration

Second configuration

Second configuration

First configuration

Second configuration

TARGETING GUIDES

CROSS-REFERENCE TO RELATED APPLICATIONS

This application is a continuation of U.S. patent application Ser. No. 17/786,868, filed Jun. 17, 2022, which is a National Stage Application, filed under 35 U.S.C. 371, of International Patent Application No. PCT/US2021/018293, filed on Feb. 17, 2021, which claims priority to U.S. Provisional Patent Application No. 62/984,043, filed on Mar. 2, 2020, the disclosure of which are is incorporated herein by reference in their entireties.

FIELD OF DISCLOSURE

The present disclosure relates to bone screw drill targeting guides that can be used in surgical procedures for correcting hallux valgus deformity.

BACKGROUND

During a minimally invasive Chevron and Akin osteotomy (MICA) procedure for correcting hallux valgus deformity, a Chevron osteotomy is made in the first metatarsal bone separating the head portion of the first metatarsal from the remainder of the metatarsal. The metatarsal head is then shifted laterally and fixed with two screws. K-wires are traditionally used to hold the metatarsal head at the intended translated position during the subsequent screw fixation procedure. Achieving the desired k-wire trajectory can be difficult. Therefore, a guiding instrument for setting the trajectory of the k-wire is desired.

SUMMARY

According to an embodiment, disclosed is a targeting guide for placing implant guides (guide wires) through two portions of a bone. The targeting guide comprises a first portion, an anchor guide, and a second portion. The first portion comprises an elongated shape defining a first end and a second end. The anchor guide is pivotally attached to the first end of the first portion by a hinge pin that defines a hinge axis, where the anchor guide is configured to be affixed to one portion of the bone by an anchoring element. The anchoring element extends along a first axis. The first axis defines an alignment plane that is orthogonal to the hinge axis. The second portion is pivotally attached to the second end of the first portion, where the second portion pivots about a pivot axis. The second portion comprises at least one guide hole sized and configured to receive a guide element therethrough, where the at least one guide hole extends through the second portion such that its longitudinal axis defines a second axis. The second axis is parallel to the alignment plane throughout the pivoting motion of the second portion.

A targeting guide for placing implant guides (guide wires) through two portions of a bone according to another embodiment is disclosed. The targeting guide comprises an elongated body that is configured to be flexible and comprises a first end and a second end. The first end is configured to be affixed to one portion of the bone by an anchoring element. The anchoring element extends along a first axis, where the first axis defines an alignment plane by the motion of the first axis when the elongated body is flexed. The second end comprises at least one guide hole sized and configured to receive a guide element therethrough, where the at least one guide hole extends through the second end such that its longitudinal axis defines a second axis. The second axis is parallel to the alignment plane throughout the flexing motion of the elongated body.

A targeting guide according to another embodiment is disclosed. The targeting guide comprises a first part and a second part. The first part comprises an elongated shape defining a first end and a second end, where the first end is configured for being inserted into an intramedullary canal of a first portion of a bone after the bone has been cut into the first portion and a second portion. The second part comprises an elongated shape defining a first end and a second end, where the first part and the second part are engaged to slide with respect to each other about an arc whereby the targeting guide can switch between a first configuration and a second configuration by pivoting relative to each other. The first end of the second part comprises a bone contacting surface for contacting and pushing the second portion of the bone off-axis relative to the first portion of the bone while the first end of the first part is inserted into the intramedullary canal of the first portion of the bone. The second end of the second part is provided with at least one guide hole extending through the second end, whereby the geometric relationship between the first end of the second part and the at least one guide hole is fixed and the at least one guide hole's longitudinal axis is aimed toward a target region defined in proximity of the bone contacting surface of the first end of the second part.

A surgical instrument kit is also disclosed, where the kit comprises at least one guide wire and a targeting guide where the targeting guide is one or more of any one of the targeting guide embodiments disclosed herein.

A method of using any one of the targeting guide embodiments disclosed herein is also disclosed.

BRIEF DESCRIPTION OF THE DRAWINGS

The inventive concepts of the present disclosure will be described in more detail in conjunction with the following drawing figures. The structures in the drawing figures are illustrated schematically and are not intended to show actual dimensions.

DETAILED DESCRIPTION

Figure 1A:
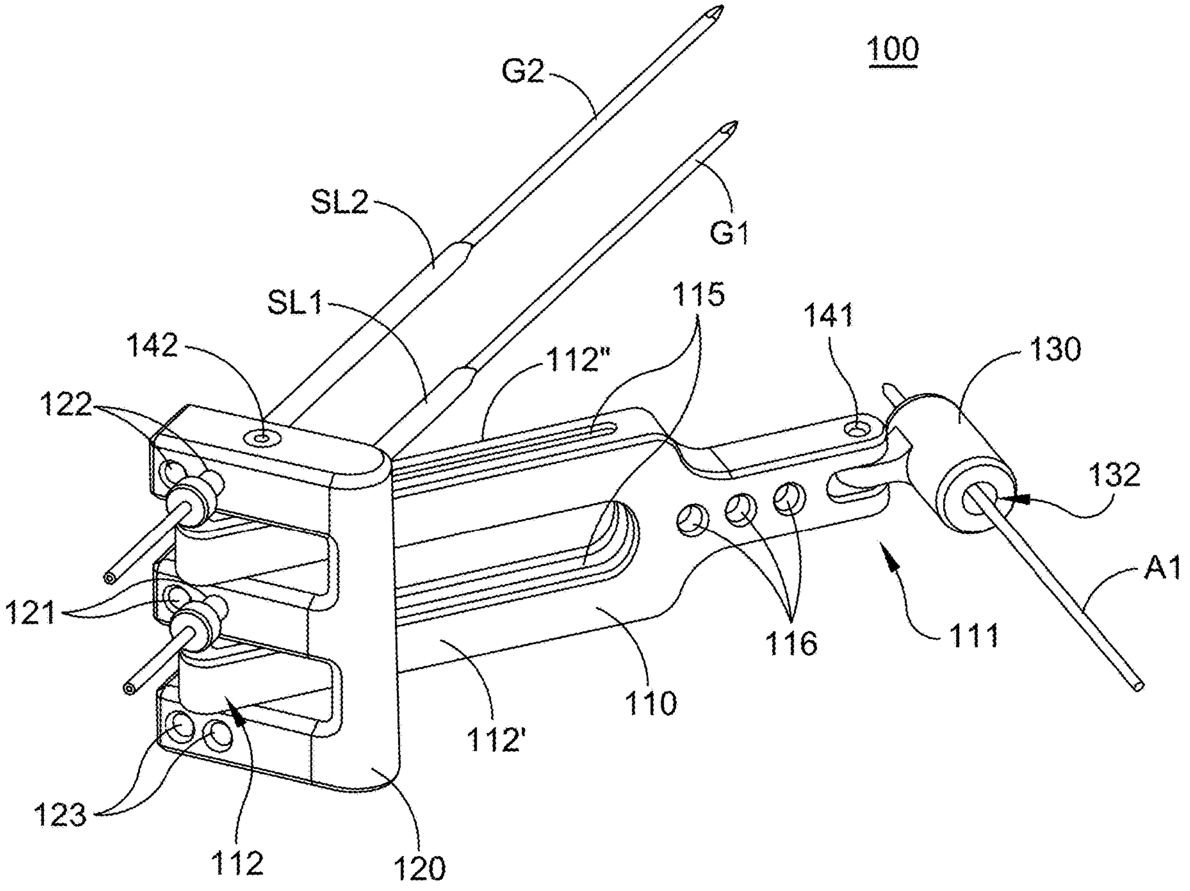
FIGS. 1A and 1B are illustrations of a targeting guide according to an embodiment.

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

Unless otherwise expressly stated, it is in no way intended that any method set forth herein be construed as requiring that its steps be performed in a specific order, nor that with any apparatus, specific orientations be required, unless specified as such. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

Figure 1B:
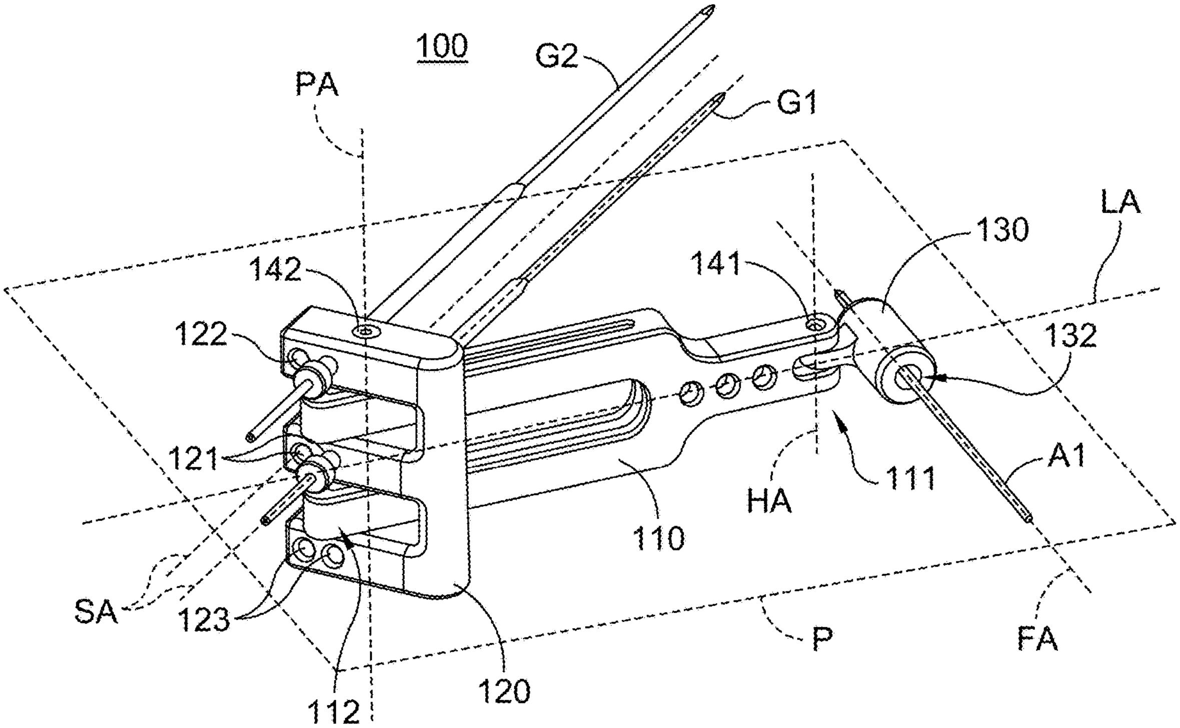

Referring to FIGS. 1A and 1B, a targeting guide 100 is disclosed for placing implant guides G1, G2 through two portions of a bone after a first metatarsal bone has been cut into a first bone portion B1 and a second bone portion B2 is disclosed. The targeting guide 100 comprises a first portion 110 comprising an elongated shape and a second portion 120. The elongated shape of the first portion 110 defines a first end 111 and a second end 112. The second portion 120 is pivotally attached to the second end 112 of the first portion 110, and an anchor guide 130 pivotally attached to the first end 111 of the first portion 110 by a hinge pin 141 that defines a hinge axis HA.

In the targeting guide embodiment 100, the first portion 110 is a rigid piece. In some embodiments, the first portion can be configured to be flexible. Such flexible piece can be comprised of a single component or multiple components. Examples of such flexible embodiments are illustrated in FIGS. 12-17.

Figure 7A:
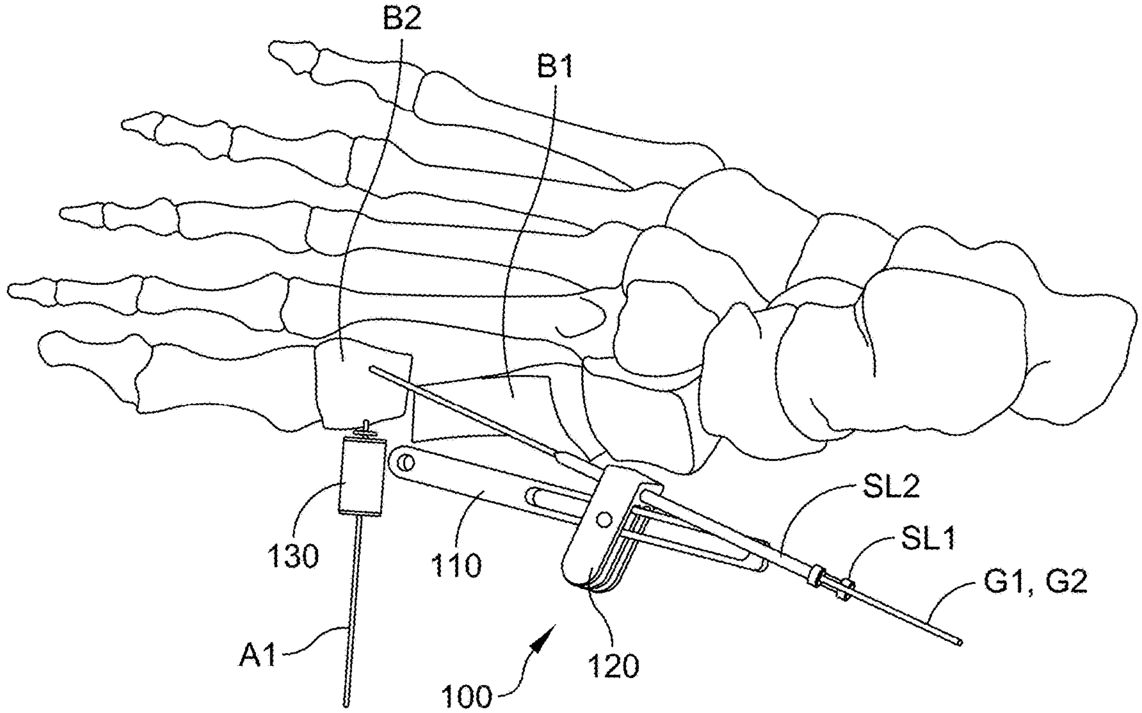
FIGS. 7A-7B are additional illustrations of the targeting guide of FIG. 1 illustrated in conjunction with a patient's foot bones to show how the device can be used in the hallux valgus correction procedure.
Figure 7B:
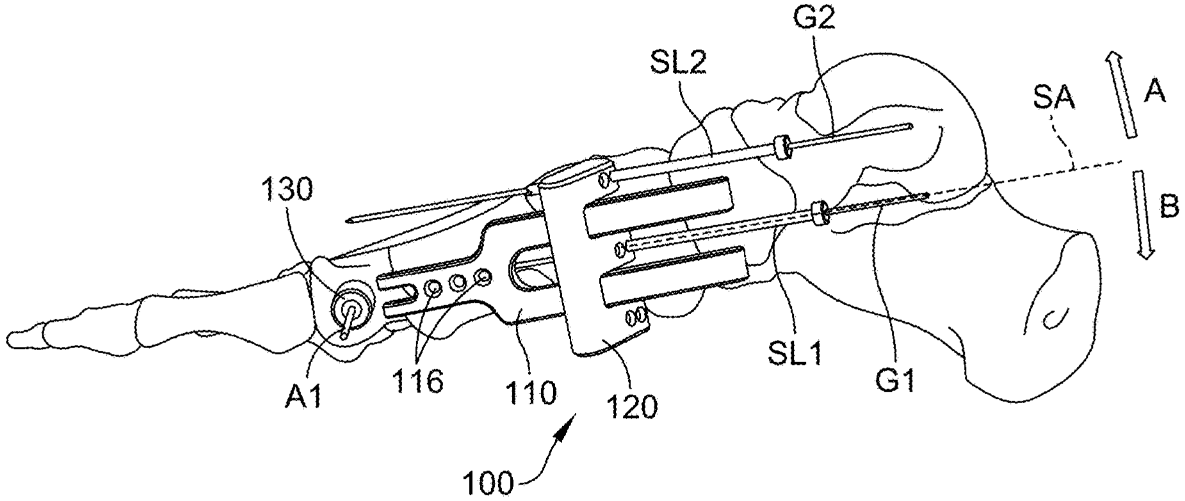

Referring to FIGS. 1A and 1B, the anchor guide 130 comprises is configured to be affixed to the second bone portion B2 (the metatarsal head) by an anchoring element A1. The anchor guide 130 comprises a channel 132 sized and configured to receive the anchoring element A1 therethrough. In an example for using the targeting guide 100, the anchoring element A1, such as an olive wire, is first placed into the second bone portion B2 at a desired location and in a desired orientation. Then, the targeting guide 100 is anchored to the second bone portion B2 by sliding the anchor guide 130 over the anchoring element A1 to arrive at a disposition such as shown in FIGS. 7A and 7B. The axis defined by the channel 132 extending through the anchor guide 130 is defined as a first axis FA and the anchoring element A1 extends along the first axis FA when the targeting guide 100 is anchored in position to the second bone portion B2. The first axis FA defines an alignment plane P that is orthogonal to the hinge axis HA.

The second portion 120 is pivotally attached to the second end 112 of the first portion 110 by a pivot pin 142 that defines a pivot axis PA. The second portion pivots about the pivot axis PA.

The second portion 120 comprises at least one guide hole 121 sized and configured to receive a guide element G1, a drill bit, a fixation pin, or a screw, therethrough. The at least one guide hole 121 extends through the second portion 120 such that the guide hole's longitudinal axis defines a second axis SA. In some embodiments, the guide element G1 can be a guide wire or a fixation pin. a guide sleeve SL. In some embodiments, the second portion 120 can have a plurality of guide holes 121. In the particular embodiment illustrated in FIG. 1A, the second portion 120 has six guide holes 121. The specific number of guide holes can vary as appropriate. In the embodiments where there are more than one guide hole, each guide hole defines a second axis SA and they are preferably all parallel to each other. In some embodiments, the guide holes are not parallel to each other. In some embodiments, some of the guide holes can be parallel to each other.

In some embodiments, the one or more guide holes 121 can be configured and adapted to be able to receive a guide sleeve SL first. Then, the guide elements G1, G2 can be inserted through the guide sleeves SL.

The second axis SA is parallel to the alignment plane P throughout the pivoting motion of the second portion 120. In some embodiments, the second axis SA lies at a distance away from the alignment plane P. In some embodiments, the second axis SA lies in the alignment plane P.

In some embodiments, because of the orthogonal relationship between the hinge axis HA of the anchor guide 130 and the alignment plane P, the first axis FA of the anchor guide 130 stays in the alignment plane P throughout the hinged motion of the anchor guide 130.

Figure 2:
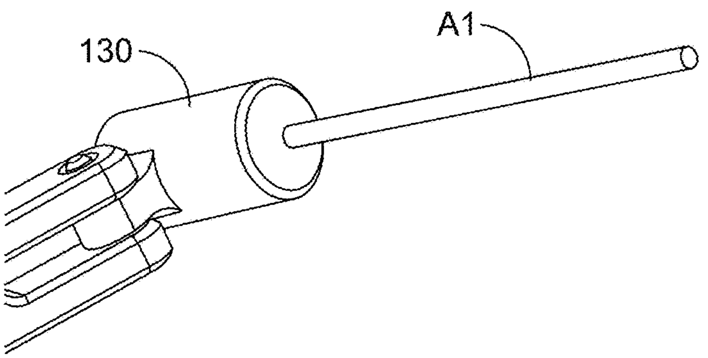
FIG. 2 is an illustration of an example of an anchor guide component of the targeting guide that has an integrally formed anchoring element.

Referring to FIG. 2, in some embodiments of the targeting guide, the anchor guide 130 can be configured with an anchoring element A1 that is permanently integrated into the anchor guide 130 (i.e. non-removable) for affixing the anchor guide 130 to a bone. The anchor guide 130 in this illustrated example and in FIG. 1A has a cylindrical shape but in other embodiments, the anchor guide can be formed to have any appropriate shape as necessary as long as it provides an anchoring element A1, whether the anchoring element is removable from the anchoring guide or integrated into it. For example, the targeting guide embodiments shown in FIGS. 14 and 17 have an anchoring guide 130 that has a disc-like shape with an integrally formed anchoring element A1.

A longitudinal axis LA of the first portion 110 of the targeting guide 100 is defined extending from the first end 111 to the second end 112 of the first portion. In some embodiments, the longitudinal axis LA intersects the hinge axis HA and the pivot axis PA.

In some embodiments of the targeting guide 100, the first portion 110 comprises at least one slot 115 that extends along a portion of the first portion 110 and the pivot pin 142 extends through the at least one slot 115, whereby the second portion 120 and the pivot pin 142 can slide along the portion of the first portion 110 in either direction defined by its longitudinal axis LA. For example, in the illustrated example shown in FIG. 1A, the first portion 110 is forked towards the second end 112 so that it has a Y-shaped section and the second end 112 bifurcates into two arms 112' and 112". Each of the two arms 112' and 112" have a slot 115 and the pivot pin 142 extends through both arms 112' and 112" via the slots 115.

In the embodiment shown in FIG. 1A, the second portion 120 is shaped like a letter "E" and has three prongs that interleaved with the bifurcated arms 112', 112" of the first portion 110. The pivot pin 142 extends through the three prongs of the E-shaped second portion 120 and the slots 115 in the interleaved arms 112', 112" of the first portion 110 so that the pivot pin 142 can slide inside the slot 115 along the portion of the length of the first portion 110 in either direction. Because the second portion 120 is connected to the pivot pin 142, the second portion 120 slides along with the pivot pin 142 in either direction.

The second portion 120 comprises one or more guide holes 121 and are all located on one side of the pivot axis PA. The one or more guide holes 121 are located and extend in a direction so that the longitudinal axis of the guide holes 121 lie in the alignment plane P of the targeting guide 100. That ensures that a guide sleeve or a guide wire placed through the guide holes 121 will lie in the alignment plane P. This is illustrated in FIGS. 1A and 1B. In the illustrated targeting guide embodiment 100, the guide holes 121 that are provided on the middle prong of the "E" shape lie in the alignment plane P. The second portion 120 can further comprise one or more guide holes 122 and 123 that do not lie in the alignment plane P. However, these additional guide holes 122, 123 extend in a trajectory that are parallel with the trajectory of the guide holes 121. Thus, guide sleeve SL2 and guide wire G2 inserted through the guide hole 122 will extend parallel to the guide sleeve SL1 and guide wire G1 inserted through the guide hole 121 as shown in FIG. 1A.

Figure 3:
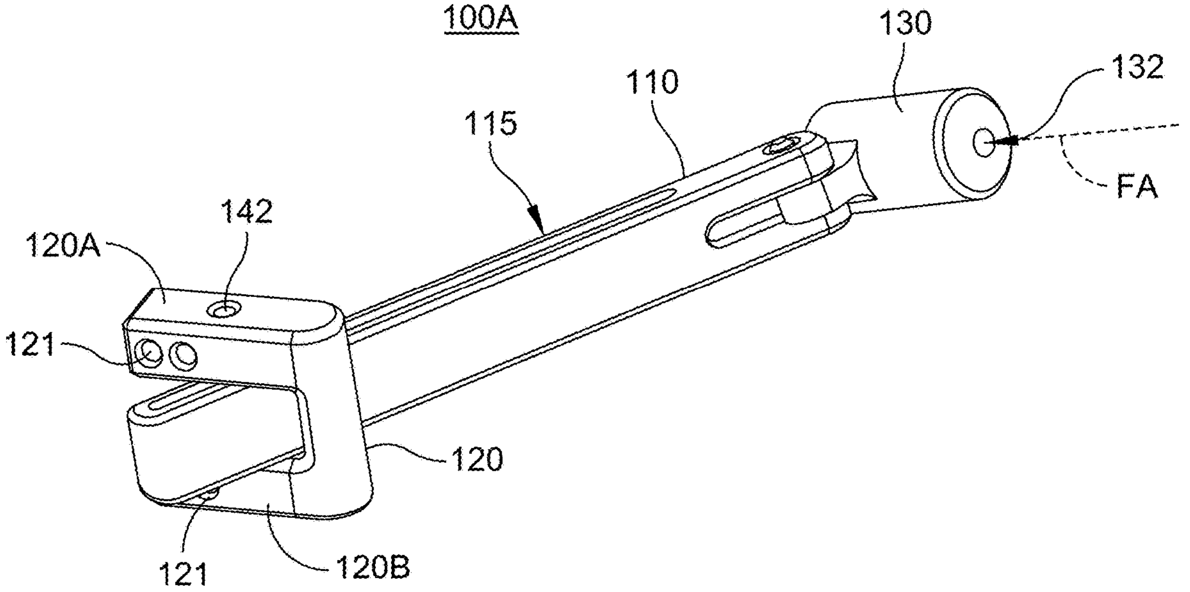
FIGS. 3-5 are illustrations of targeting guides according to other embodiments.

In another example of the targeting guide 100A shown in FIG. 3, the first portion 110 is a straight piece that is not bifurcated and has one slot 115 that extends along a portion of the length of the first portion 110. The second portion 120 is bifurcated with two prongs 120A and 120B. The pivot pin 142 extends from prong 120A to the second prong 120B through the one slot 115. The pivot pin 142 can slide within the slot 115. Thus, the position of the second portion 120 along the first portion 110 can be adjusted by sliding the second portion 120 along a portion of the length of the first portion 110 in either direction. Each of the prongs 120A, 120B comprises one or more guide holes 121. The guide holes 121 in one of the two prongs 120A, 120B are located and extend in a direction so that the longitudinal axes of the guide holes 121 in each of the prongs 120A and 120B in combination with the first axis FA defined by the channel 132 define an alignment plane P of the targeting guide 100A. In other words, in the targeting guide 100A example, two alignment planes P are defined: one alignment plane defined by the longitudinal axes of the two guide holes 121 on the first prong 120A and the first axis FA; and a second alignment plane defined by the longitudinal axes of the two guide holes 121 on the second prong 120B and the first axis FA. Thus, after the anchor guide 130 is anchored to the second bone portion B2 using an anchoring element A1, the surgeon can select between the two sets of the guide holes 121 on the prongs 120A, 120B to use for targeting the holes for bone screws by pivoting the targeting guide 100A about the first axis FA defined by the anchoring element A1.

Figure 4:
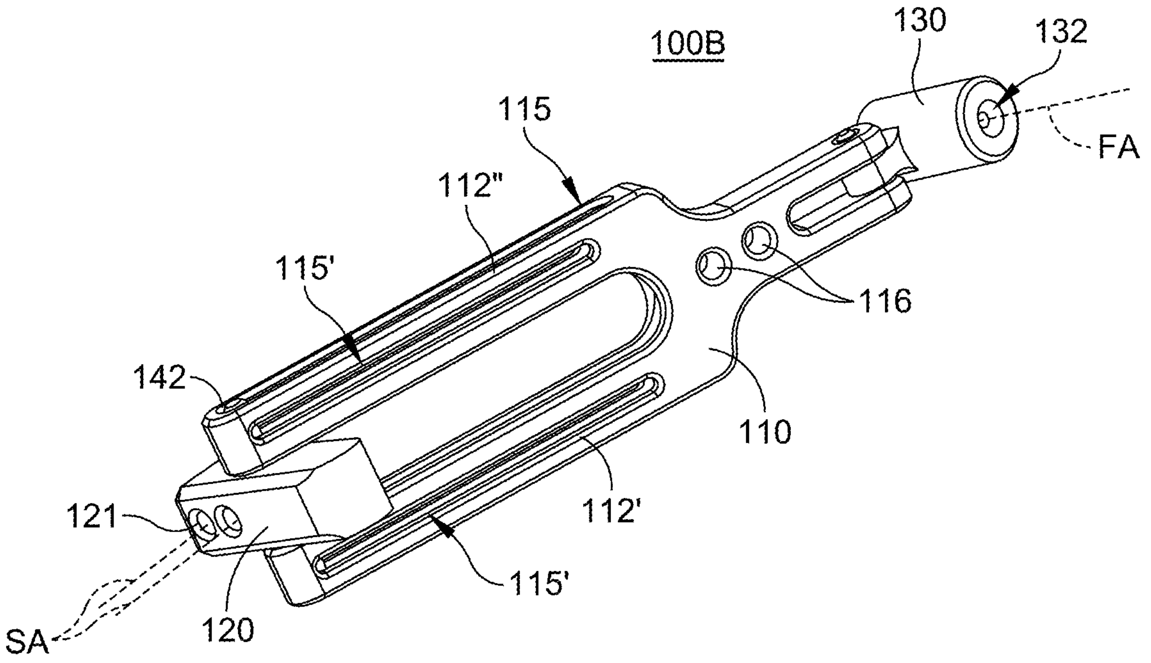
Figure 5:
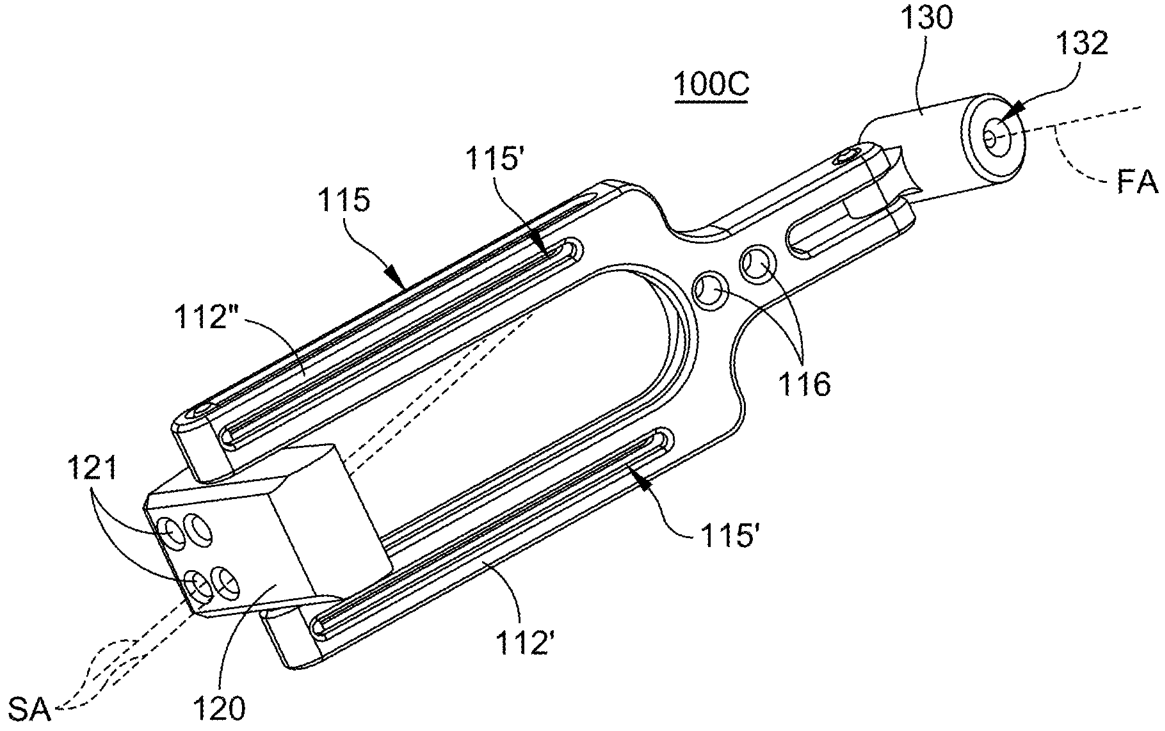

Alternatively, as shown in the targeting guide embodiments 100B and 100C shown in FIGS. 4 and 5, respectively, the second portion 120 can have a simpler shape that does not have any prongs. In these embodiments, the second portion 120 is positioned between the two arms 112', 112" of the first portion 110. A pivot pin 142 extends from one arm 112' to the other arm 112" through the slots 115 and through the second portion 120 thus allowing the second portion 120 to slide along a portion of the length of the first portion 110 in either direction. The second portion 120 can be provided with one or more guide holes 121 that are located and extend in a direction so that the longitudinal axes of the guide holes 121 lie in the alignment plane P of the targeting guides 100B, 100C. That ensures that a guide sleeve or a guide wire placed through the guide holes 121 will lie in the alignment plane P. Referring to the targeting guide 100C which has two pairs of guide holes 121, this embodiment will be configured to define two alignment planes P similar to the targeting guide 100A described above. The first alignment plane defined by the first axis FA and the second axes SA defined by one of the two pairs of guide holes 121, and the second alignment plane defined by the first axis FA and the second axes SA defined by the other of the two pairs of guide holes 121.

Figure 26:
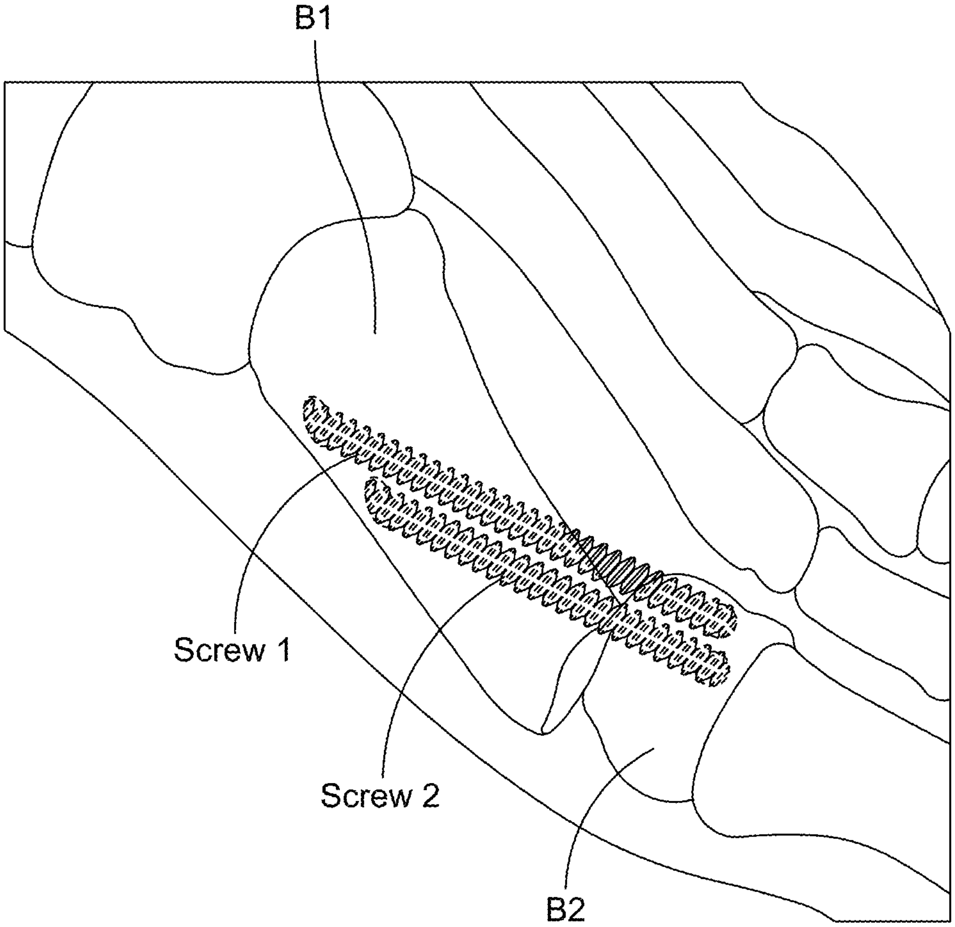
FIG. 26 is an illustration showing the secured dispositions of the two bone portions of a metatarsal after a hallux valgus correction procedure assisted by the targeting guide of the present disclosure is completed.

In the targeting guide embodiments 100, 100A, 100B, 100C, the pivoting capability of the second portion 120 allows the surgeon to adjust the trajectory of the guide sleeve SL1 and the guide wire G1 inserted through one of the guide holes 121 so that the trajectory extends through the two bone portions B1 and B2 as shown in FIG. 7A. That trajectory represents the trajectory for the bone screw that will be threaded through the two bone portions B1 and B2 to fix the disposition of the two bone portions as shown in FIG. 26.

Referring to FIGS. 4 and 5, the first portion 110 of the targeting guide embodiments 100, 100A, 100B, 100C can further comprise secondary slots 115' along its length that allow one or more anchoring elements such as K-wires to be inserted through the secondary slots 115' and into the patient's foot, thus, anchoring the first portion 110 to the foot once it is oriented as desired. As shown, the secondary slots 115' are oriented orthogonal to the slots 115 so that the anchoring elements placed through the secondary slots 115' will extend generally parallel to the alignment plane P (see FIG. 1B). The first portion 110 can further comprise additional anchoring holes 116 that allow one or more anchoring elements such as K-wires to be inserted there through and into the patient's foot for anchoring the targeting guide as appropriate.

Figure 6:
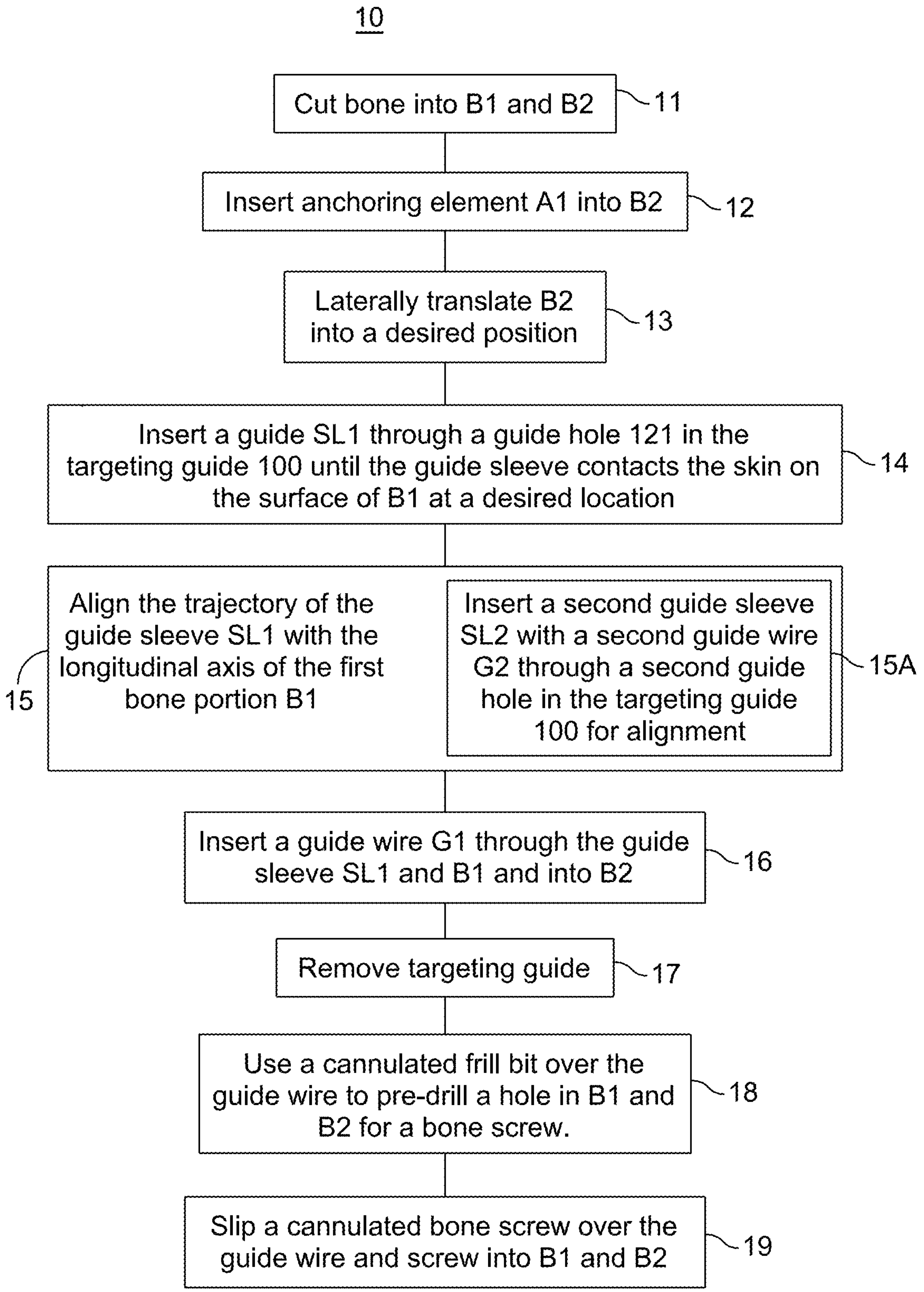
FIG. 6 is a flowchart illustrating a method of using a targeting guide of one embodiment.

Referring to the flow chart 10 shown in FIG. 6, a method of using the targeting guide 100A, 100B, or 100C is disclosed. The method comprises an osteotomy cutting a bone into the first B1 and second B2 portions. (See Step 11). This can be a chevron osteotomy or a transverse osteotomy conducted as a minimally invasive procedure through a small (3-5 mm) percutaneous incision. In the illustrated example the bone is a first metatarsal bone and the procedure is for treating hallux valgus deformity. Next, an anchoring element A1 held by the anchor guide 130 is inserted into the second bone portion B2 (the metatarsal head fragment) to anchor the first end 111 of the first portion 110 of the targeting guide 100A, 100B, or 100C. (See Step 12). Preferably, the anchoring element A1 is inserted into the second bone portion B2 as close to the center of the diameter of the bone such that the longitudinal axis of the metatarsal bone lies substantially in the alignment plane P of the targeting guide 100A, 100B, or 100C. Being substantially in the alignment plane P refers to being exactly in the alignment plane P or close to being exactly in the alignment plane P. As a surgical procedure goes, the closer it is to being exactly in the alignment plane P the more desired it will be. Next, the second portion B2 of the bone is laterally translated into a desired position. (See Step 13). Next, at least one guide sleeve SL1 is inserted through the at least one guide hole 121 (the guide hole that lies in the alignment plane P of the targeting guide) in the second part 120 toward the first bone portion B1 until the guide sleeve SL1 contacts the patient's skin. (See Step 14). Next, the trajectory of the guide sleeve SL1 is aligned with the longitudinal axis of the first bone portion B1 (the metatarsal shaft fragment) in the dorsal-plantar direction. (See Step 15). Referring to FIG. 7B, this alignment is achieved by rotating the targeting guide 100A, 100B, or 100C about the anchoring element A1 in the dorsal direction (noted by arrow A) or the plantar direction (noted by arrow B) and visually align the guide sleeve SL1 to the longitudinal axis of the metatarsal in the dorsal-plantar direction. The trajectory of the guide sleeve SL1 is represented by the second axis SA of the guide hole 121. This alignment step aligns the guide sleeve SL1 so that the guide sleeve SL1 lies in the alignment plane P. Since the trajectory of the guide sleeve SL1 defines the trajectory for the bone screw that will be placed through the bone portions B1 and B2 later, this will ensure that the subsequently placed bone screw will be placed through the middle (in the dorsal-plantar direction) of the bone. The trajectory of the guide sleeve SL1 is represented by the longitudinal axes SA illustrated in FIGS. 1B and 7B. After the guide sleeve SL1 is aligned as desired, the guide sleeve SL1 defines a channel that will guide a guide wire G1 or a drill bit for drilling into B1 and B2.

At this point, an optional but preferred procedure will be described. Referring to the side view shown in FIG. 7B, as a preferred option, a second guide sleeve SL2 holding a second guide wire G2 can be inserted through another guide hole 121 along with the installation of the first guide sleeve SL1. The second guide sleeve SL2 is inserted through a guide hole 121 that is located above the first guide hole 121 through which the first guide sleeve SL1 has been placed. As shown in FIGS. 7A and 7B, in this arrangement, the second guide wire G2 is parallel with the first guide sleeve SL1 and is located above the first guide sleeve SL1 and also above the patient's foot. Therefore, the surgeon can use the second guide wire G2 as a visual or fluoroscopic alignment guide to aim the trajectory SA of the first guide wire G1 which will be placed through the first guide sleeve SL1 and through the two bone portions B1, B2. (See Step 14A).

Next, a guide wire G1 is inserted through the guide sleeve SL1 from the end away from the first bone portion B1 and advanced into and through the first bone portion B1 and into the second bone portion B2. (See Step 15). The guide wire G1 penetrates into the second bone portion B2 but does not go all the way through the second bone portion B2.

Next, the targeting guide 100 is removed leaving the guide wire G1 in place in the bone portions B1, B2. (See Step 16). At this point, the use of the targeting guide 100 is completed. Next, in order to complete the hallux valgus repair procedure a cannulated drill bit is used over the guide wire G1 to pre-drill a hole in B1 and B2 for a bone screw. (See Step 17). Next, a cannulated bone screw is slipped over the guide wire G1 and screwed into and through the first bone portion B1 and into the second bone portion B2, thus securing the two bone portions B1 and B2 in the new disposition. (See Step 18). The secured disposition of the bone portions B1 and B2 is shown in FIG. 26.

Referring to FIGS. 8-11, a targeting guide 100D for placing implant guides G1 through two portions of a bone such as a first metatarsal after the first metatarsal has been cut into a first bone portion B1 (the metatarsal shaft portion) and a second bone portion B2 (the metatarsal head portion) according to another embodiment is disclosed. The targeting guide 100A is constructed in a similar manner to the targeting guide 100 and comprises the same components with the exception being the configuration of the anchor guide 130A in the targeting guide 100A.

The targeting guide 100 is configured to be anchored to the second bone portion B2 before the second bone portion B2 is laterally translated. And once the targeting guide 100 is anchored, the targeting guide 100 can be rotated about the anchoring element A1, allowing the second end 112 of the targeting guide 100 to translate dorsally or plantarly. The targeting guide 100D, however, is configured to be anchored to the surgical site after the second bone portion B2 has been first laterally translated into a desired position and the two bone portions B1 and B2 are temporarily fixed in the translated arrangement by a pair of anchoring elements A1, A2. The anchoring elements A1, A2 in this case can be appropriate fixation pins such as olive wires. The temporary fixation using two anchoring elements A1, A2 is carried out using another instrument first. Once the two anchoring elements A1, A2 are in place, then, the targeting guide 100D is anchored to the surgical site by sliding the anchor guide 130A over the two anchoring elements A1, A2, thus, resulting in the configuration shown in FIG. 8. Then, the targeting guide 100D is used to guide bone screws to permanently fix the two bone portions B1 and B2. That procedure will be described in more detail below.

Temporarily fixing the disposition of the two bone portions B1 and B2 mentioned above can be carried out using a targeting guide 400 shown in FIGS. 28A-28D. The targeting guide 400 comprises an elongated handle portion 405 and a bifurcated working end 402. The bifurcated working end comprises a translator part 410 and a guide part 420. The translator part 410 can be a needle-like extension that is pointed to be inserted into the intramedullary canal of the cut end of the first bone portion B1 (the metatarsal shaft fragment). The guide part 420 extends in-line with the translator part 410, extends beyond the tip of the translator part 410. At the end of the guide part 420 comprises one or more guide holes 421 that are oriented for guiding one or more anchoring elements A1, A2 through the two bone portions B1, B2 when the translator part 410 is fully inserted into the intramedullary canal of the first bone portion B1. The anchoring elements A1, A2 are intended to temporarily hold the two bone portions B1, B2 in position to allow the use of the targeting guide 100D to place bone screws for affixing the two bone portions B1, B2 permanently. In the illustrated example, the guide part 420 comprises two guide holes 421.

Figure 28A:
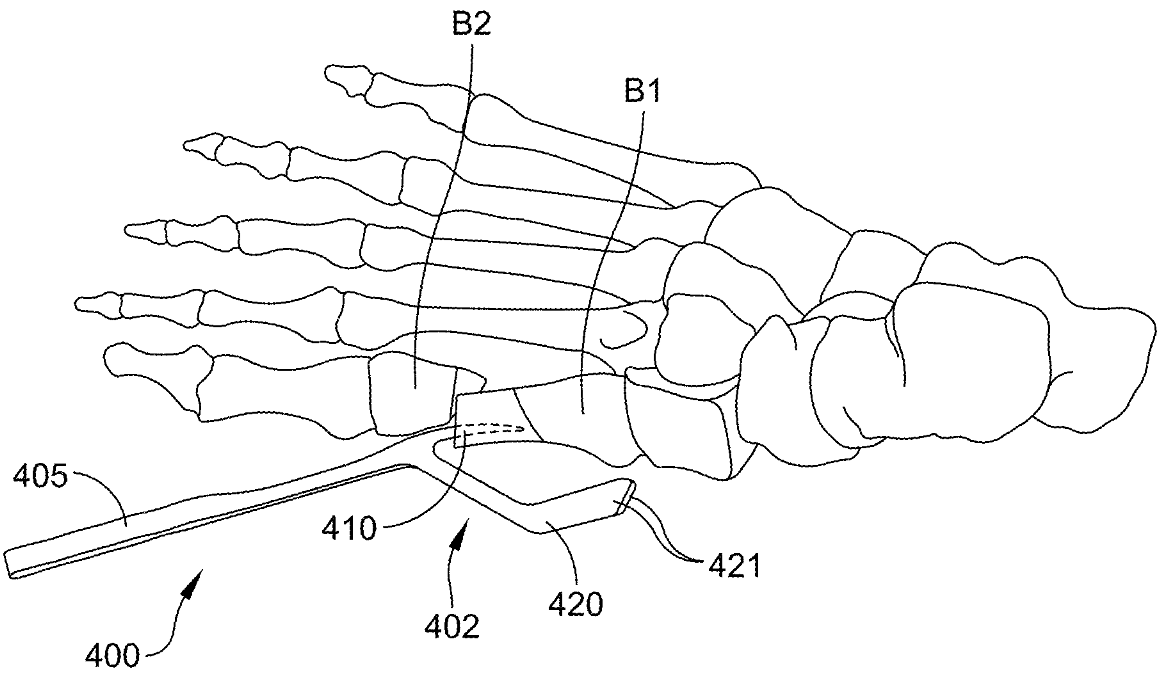
FIGS. 28A-28D are illustrations showing another embodiment of a targeting guide.
Figure 28B:
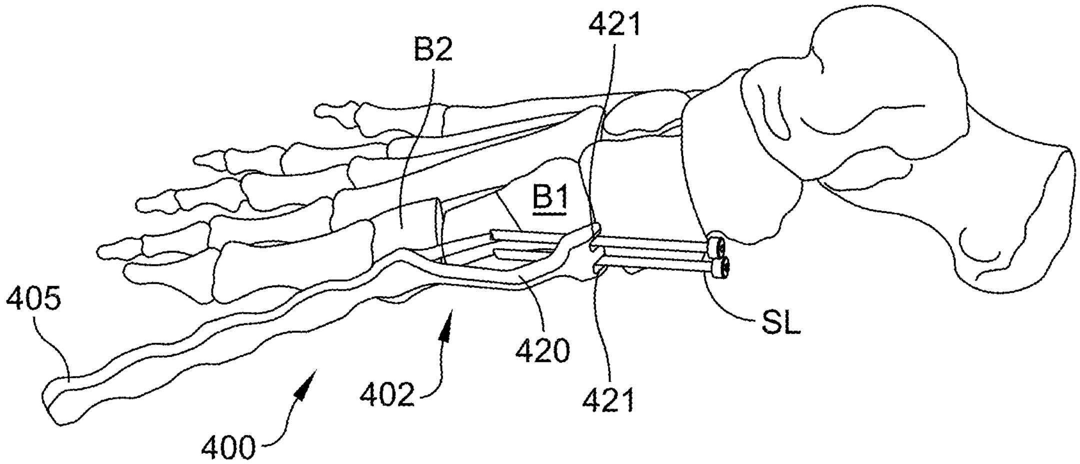
Figure 28C:
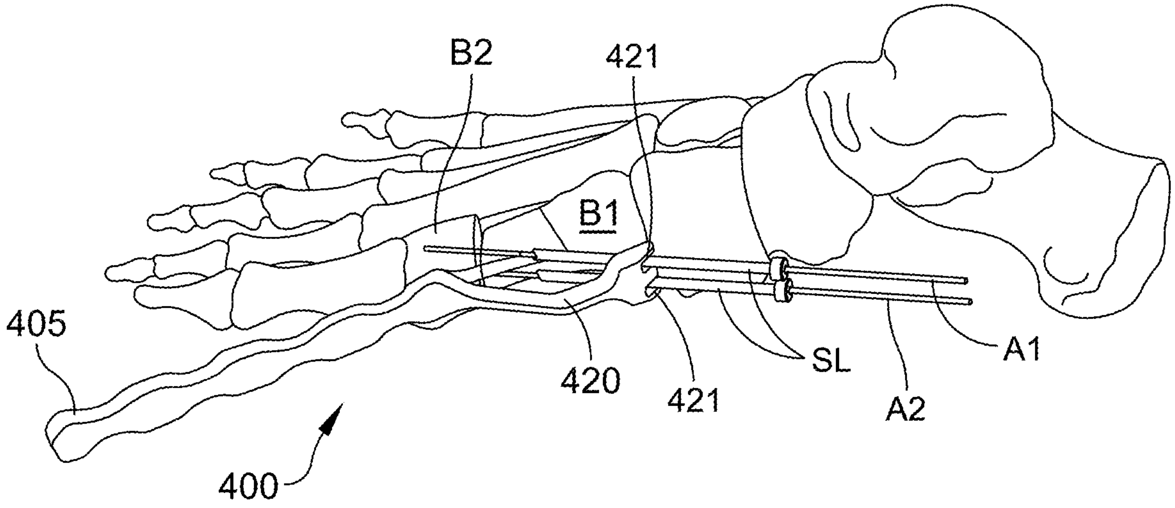
Figure 28D:
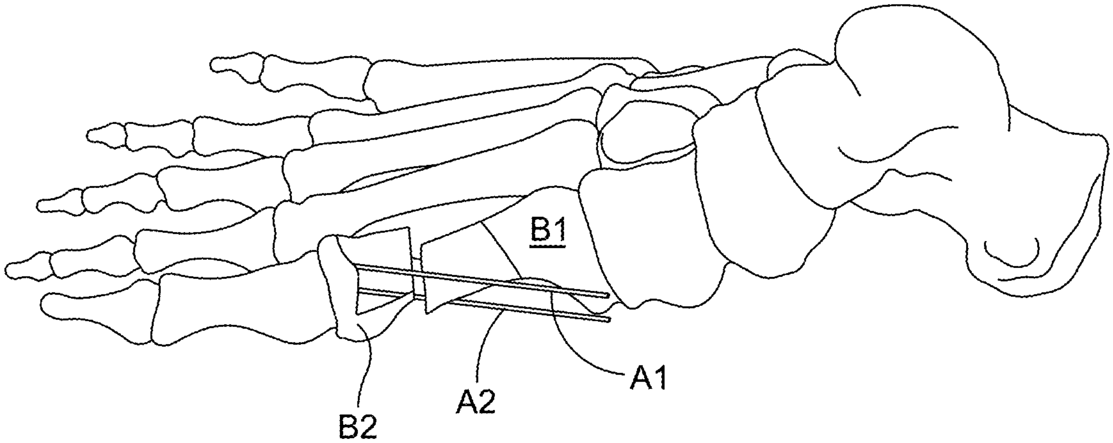

After an MIS osteotomy (can be a chevron osteotomy or a transverse osteotomy) is performed on a metatarsal bone and cut into two portions B1 and B2, the translator part 410 is inserted into the intramedullary canal of the first bone portion B1 (the shaft portion of the metatarsal). Then, using the translator part 410 as a fulcrum the surgeon can move the handle 405 in the medial-lateral direction to push and translate the second bone portion B2 (the head of the metatarsal) in lateral direction as shown in FIG. 28A. With the two bone portions B1, B2 in the desired configuration for correcting hallux valgus, a pair of anchoring elements A1, A2 are inserted through the guide holes 421 and thrown through the two bone portions B1 and B2 to temporarily fix them in that configuration. The anchoring elements A1, A2 can be ones of a variety of suitable fixation pins or K-wires. The anchoring elements A1, A2 can be inserted directly through the guide holes 421 or alternatively, guide sleeves SL can be used as shown in FIGS. 28B, 28C. Once the anchoring elements A1, A2 are in place, the targeting guide 400 can be removed. FIG. 28D shows the two anchoring elements A1, A2 in place. At this point, the anchoring elements A1, A2 are just being placed to hold the two bone portions B1, B2 in place and the anchoring elements A1, A2 do not represent the locations where bone screws will be placed for permanently holding the two bone portion s B1, B2 together.

After the targeting guide 400 is used to place the two anchoring elements A1, A2 through the two bone portions B1, B2, the targeting guide 100D is used to target and place two bone screws through the first and second bone portions B1 and B2 for permanently fixing the two bone portions in their new positions.

Figure 8:
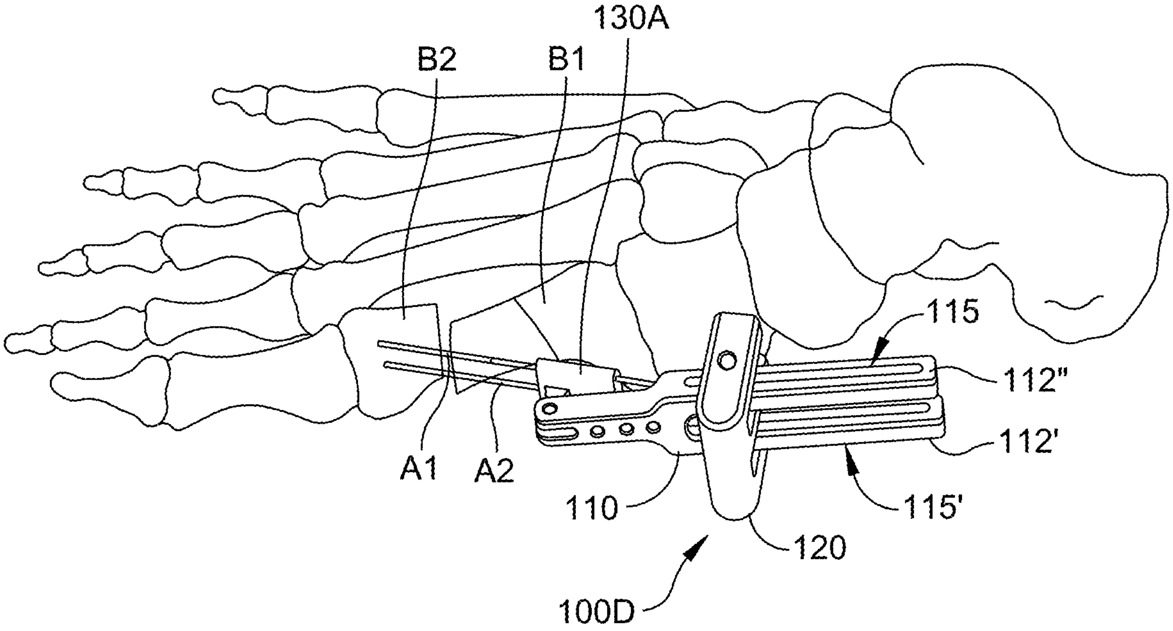
FIGS. 8-17 are illustrations of targeting guides according to other embodiments.

At this point, the targeting guide 100D is anchored to the second bone portion B2 by sliding the anchor guide 130A over the two anchoring elements A1, A2 as shown in FIG. 8. The anchor guide 130A comprises two holes for receiving the anchoring elements A1, A2. The two anchoring elements A1, A2 are positioned so that they are parallel to each other but spaced apart in dorsal-plantar direction. This configuration provides more stability to the targeting guide 100D because the two anchoring elements prevent the targeting guide 100D from rotating.

Figure 9:
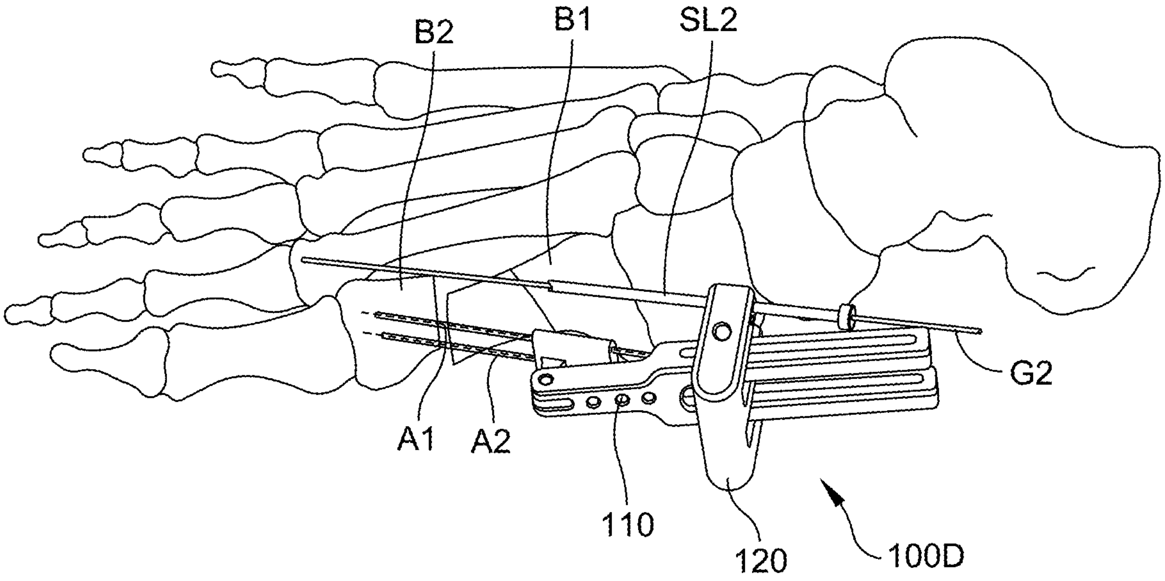
Figure 10:
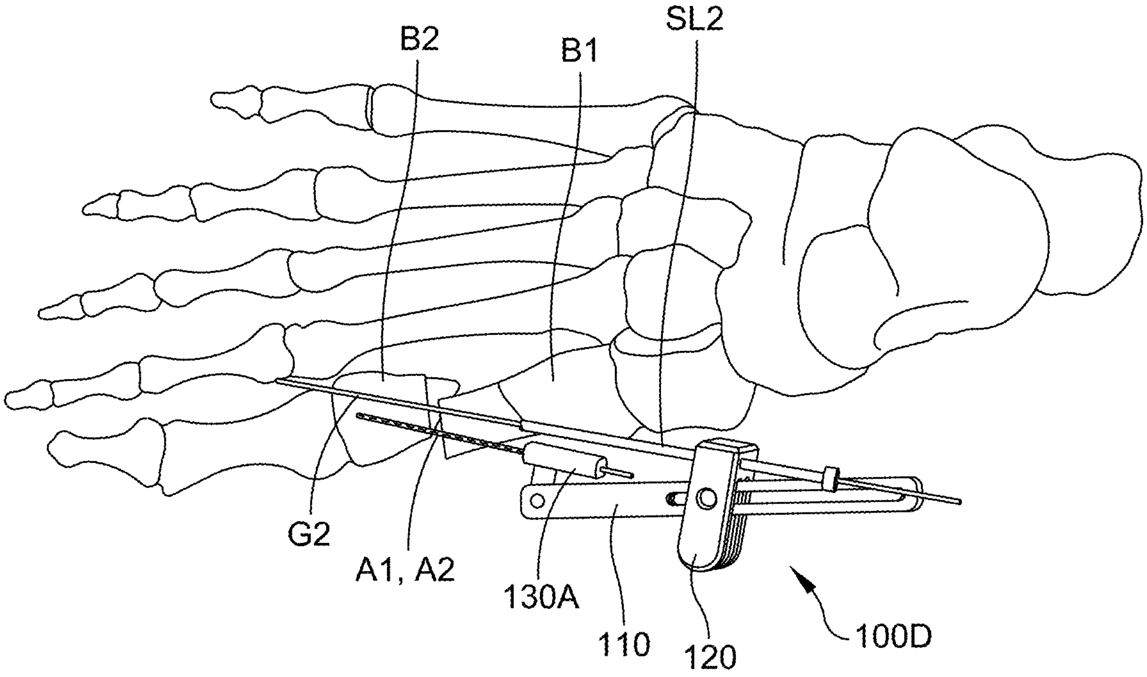
Figure 11:
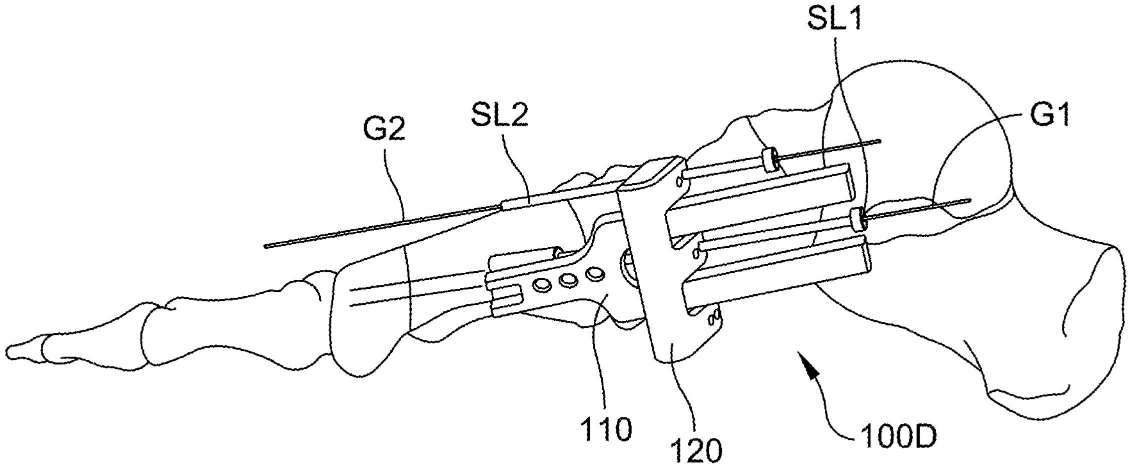

As mentioned above, the targeting guide 100D has the same structure as the targeting guide embodiment 100 except for the anchor guide 130A. The anchor guide 130A is pivotally attached to the first portion 110 so that the targeting guide 100D can be placed into the configuration shown in FIG. 8. In this configuration, the first portion 110 and the second portion 120 can be used in the manner described above in connection with the embodiment of the targeting guide 100 to throw one or more guide elements G1, G2 through the two bone portions B1, B2 in a desired orientation and location as shown in FIGS. 9-10. As with the targeting guide 100, the two guide elements G1, G2 can be directly inserted through the guide holes 121 provided in the second portion 120. Alternatively, guide sleeves SL can be first inserted through the guide holes 121 and the two guide elements G1, G2 can be inserted through the guide sleeves SL. FIGS. 9-11 illustrate the examples where the guide sleeves SL are utilized. As explained in connection with the embodiment of the targeting guide 100, one of the guide elements G2 can be inserted through one of the guide hole 121 that is not in the alignment plane P such that the guide element G2 hovers over the patients foot as shown in FIG. 9. This guide element G2 can be used as a reference under fluoroscopy that shows the trajectory of the guide element G1 that is being thrown through the two bone portions B1, B2.

For example, in the example shown in FIGS. 9 and 11, the first guide element G1 is guided by the guide hole 121 in the middle prong of the "E" shaped second portion 120 and the second guide element G2 is guided by the guide hole 122 in an outer prong of the "E" shaped second portion 120. The guide hole 121 in the middle prong of the second portion defines a second axis SA that lies in the alignment plane P (see FIG. 2) and the first guide element G1 is driven through the two bone portions B1, B2. The guide hole 122 in the outer prong of the "E" shaped second portion 120 defines a second axis SA that lies at a distance away from but parallel to the alignment plane P. As shown in the FIGS. 9 and 10, the guide hole 122 is in the particular outer prong of the "E" shaped second portion 120 that is on the dorsal side of the patient's foot so that the second guide element G2 hovers over the two bone portions B1, B2. Because the second guide element G2 is parallel with the first guide element G1, the guide element G2 can be used as a reference under fluoroscopy that shows the trajectory of the first guide element G1 that gets inserted through the two bone portions.

After the guide elements G1, G2 are in place, the targeting guide 100D can be removed and a cannulated drill bit can be used over the first guide element G1 to pre-drill a hole through B1 and into B2 for receiving a bone screw. Next, a cannulated bone screw is slipped over the guide element G1 and screwed into and through the first bone portion B1 and into the second bone portion B2, thus securing the two bone portions B1 and B2 in their new secured disposition. The secured disposition of the bone portions B1 and B2 is shown in FIG. 26. The description above only mentioned one guide element G1 as being in the alignment plane P and being thrown through the two bone portions B1, B2, however, more than one guide elements can be thrown into the two bone portions B1, B2 to drill the bones and thread additional bone screws to secure the two bone portions B1, B2. This can be achieved by utilizing additional guide holes 121 that are in the alignment plane P among the one or more guide holes 121 provided in the second portion 120.

In the targeting guide embodiments 100 and 100A, the first portion 110 is a rigid piece. In some embodiments, the first portion can be configured to be flexible. Such flexible piece can comprise a single component or multiple components. Such flexible embodiment is illustrated in FIGS. 12-18.

Figure 12:
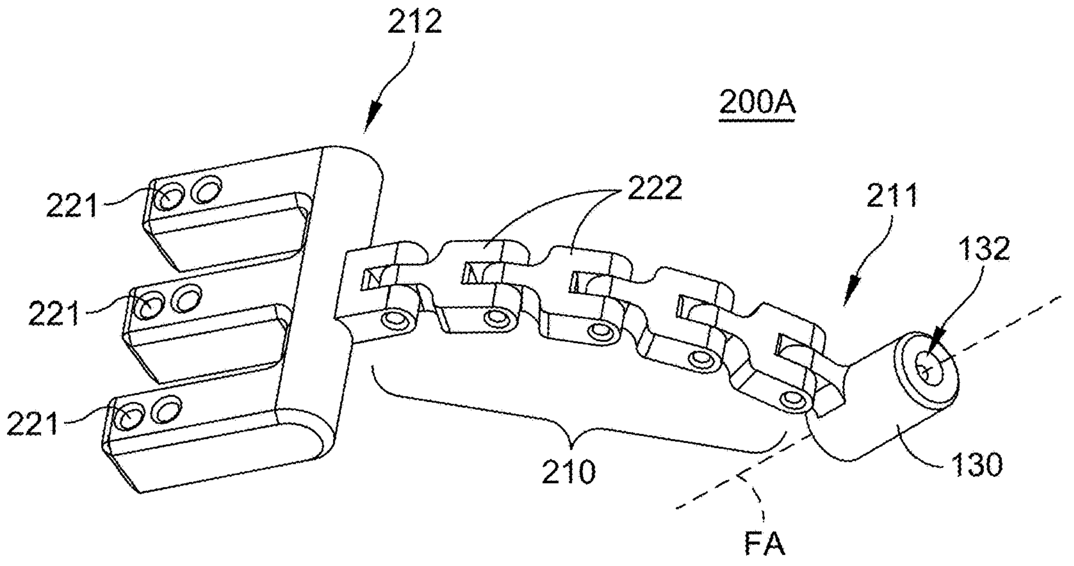

Referring to FIG. 12, a targeting guide 200 for placing implant guides G1 through two portions of a bone after a first metatarsal bone has been cut into a first bone portion B1 and a second bone portion B2 is disclosed. The targeting guide 200 comprises an elongated body 210 that is configured to be flexible and comprising a first end 211 and a second end 212. The first end 211 is configured to be affixed to one portion of the bone by an anchoring element 130. The anchoring element 130 extends along a first axis FA. The first axis FA defines an alignment plane P by the anchoring element's range of motion. The second end 212 comprises at least one guide hole 221 sized and configured to receive a guide element G1 (e.g. guide wire) or a guide sleeve SL therethrough, where each of the at least one guide hole 221 extends through the second end 212 such that its longitudinal axis defines a second axis SA. When there are more than one guide hole 221, the second axes SA are parallel to each other. The second axes SA are parallel to the alignment plane P throughout the flexing motion of the elongated body.

Figure 13:
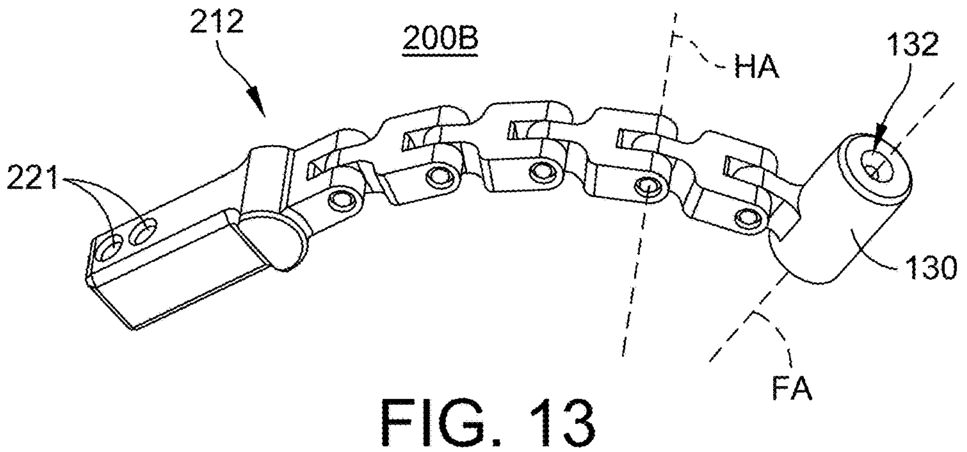
Figure 14:
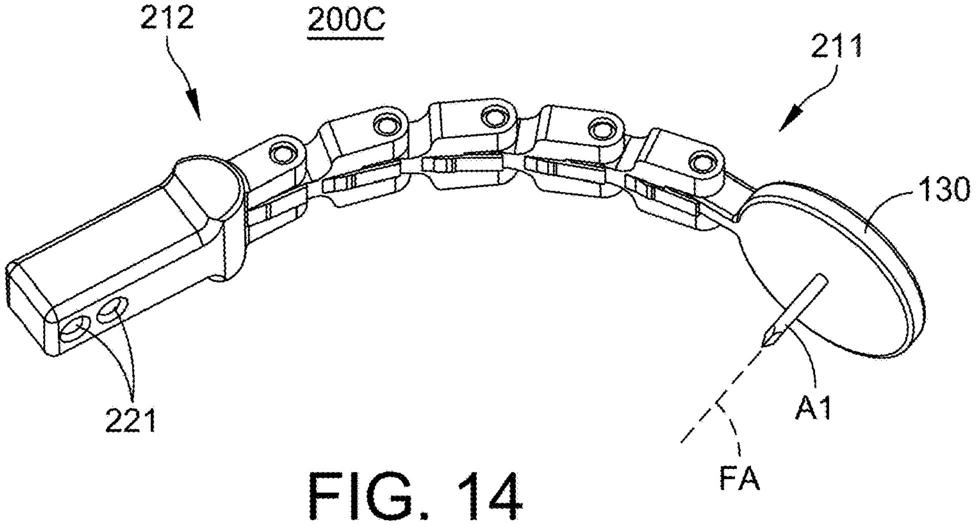
Figure 15:
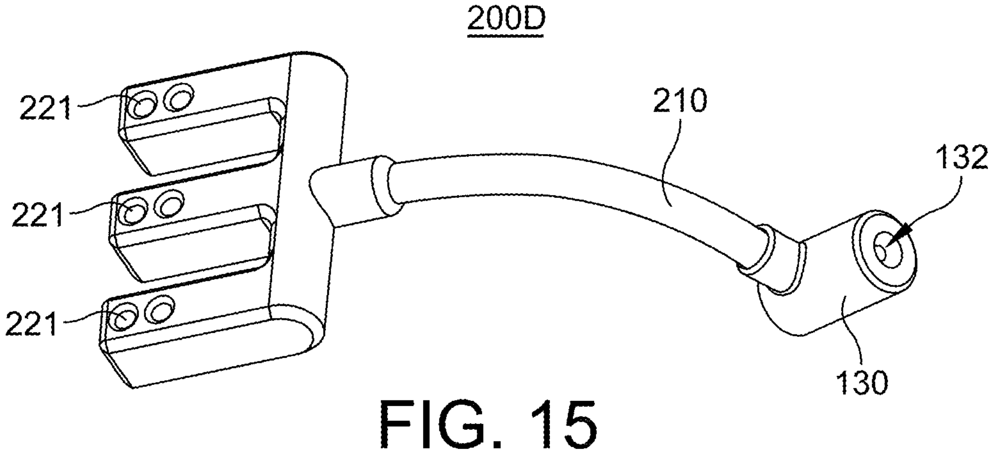
Figure 16:
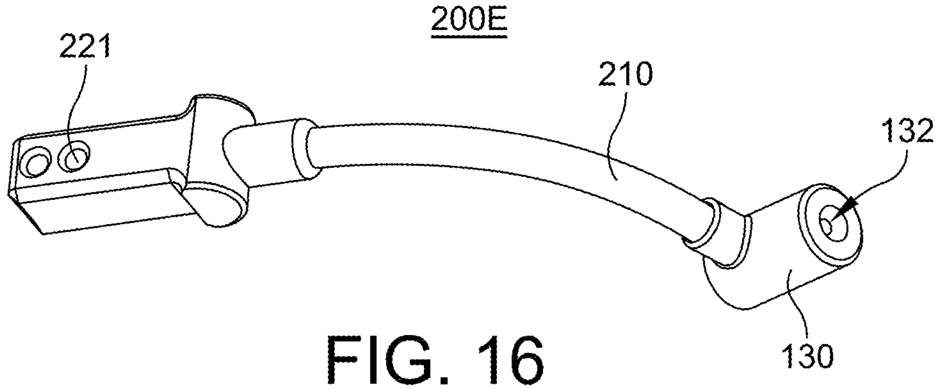
Figure 17:
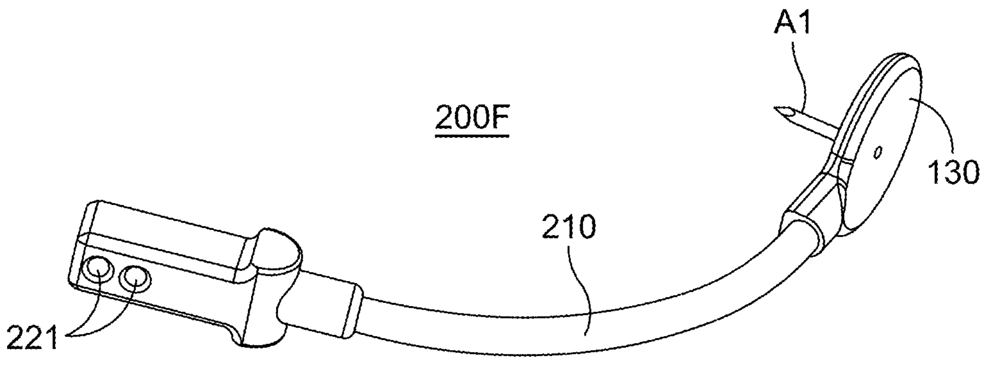

In some embodiments, illustrated by the targeting guide 200 shown in FIGS. 12-14, the elongated body 210 can be an assembly of a plurality of segments that are pivotally connected to each other as shown. In some embodiments, illustrated by the targeting guide 200A shown in FIGS. 15-17, the elongated body 210 can be configured as a continuous flexible piece. Such unitary flexible elongated body can be made of a flexible polymer material. Such polymer material can be a solid single polymer or configured with a composite structure. An example of a composite structure is a coil spring core that is coated with a polymer material.

Figure 18:
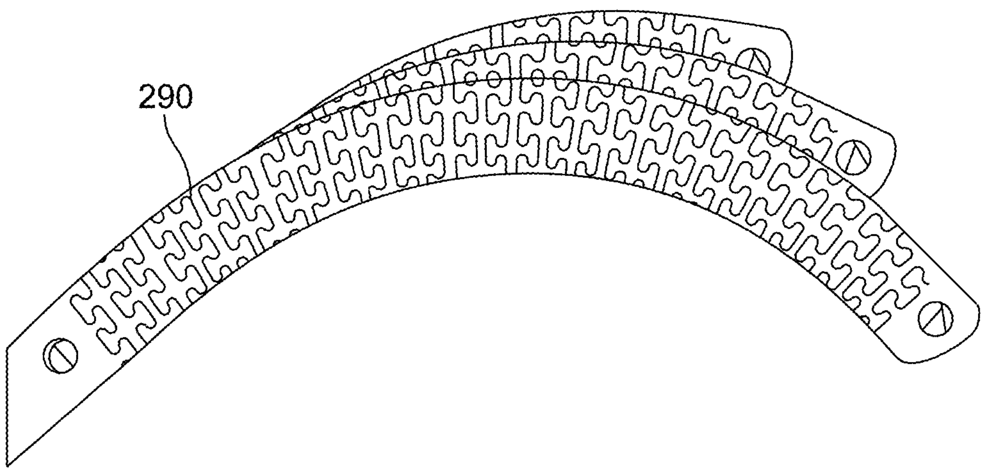
FIG. 18 is an illustration of an example of commercially available flexible shaft component.

Referring to FIG. 18, in some embodiments, the flexible elongated body 210 can be a metal tube that is cut to allow flexing. The illustrated example is a structure available from Avalign Technologies, Inc. of Bannockburn, IL, U.S.A. The laser cut pattern 290 allows the elongated body 210 to flex.

Figure 19:
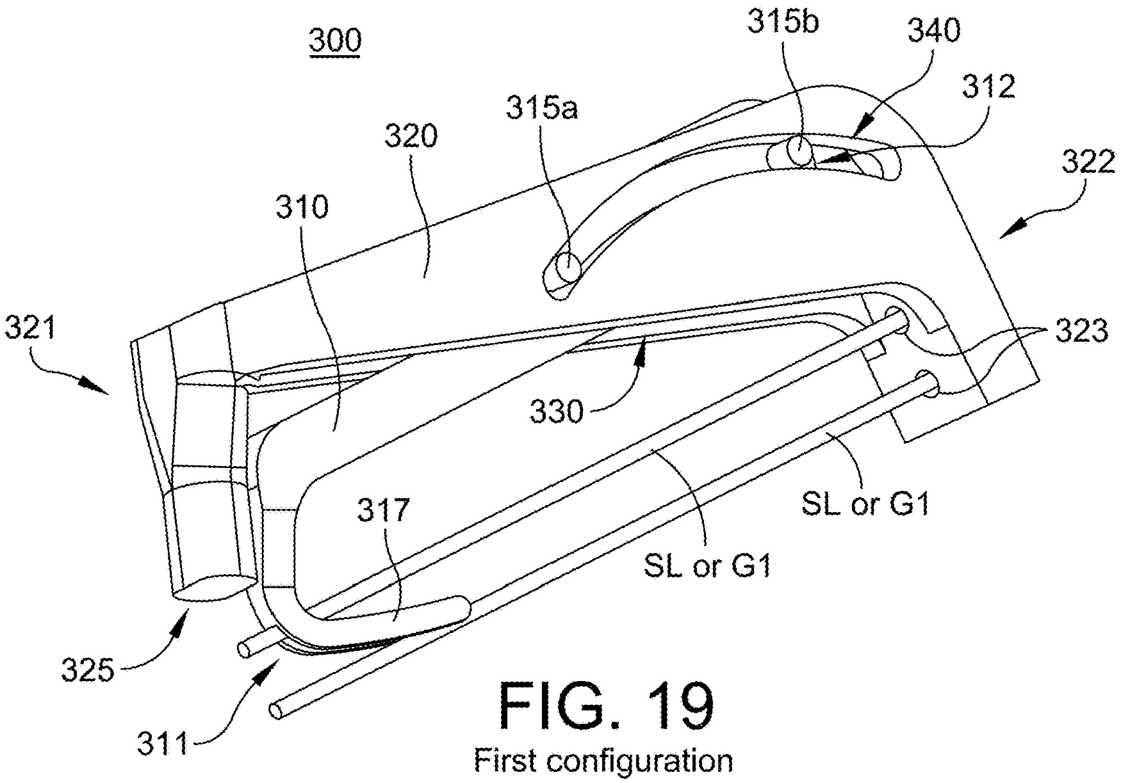
FIGS. 19-22 are illustrations of a targeting guide according to another embodiment.

Referring to FIG. 19, a targeting guide 300 for placing guide element G1 through two portions of a bone after a first metatarsal bone has been cut into a first bone portion B1 and a second bone portion B2 is disclosed. According to some embodiments, the targeting guide 300 comprises a first portion 310 comprising an elongated shape defining a first end 311 and a second end 312, and a second portion 320 comprising an elongated shape defining a first end 321 and a second end 322.

Figure 20:
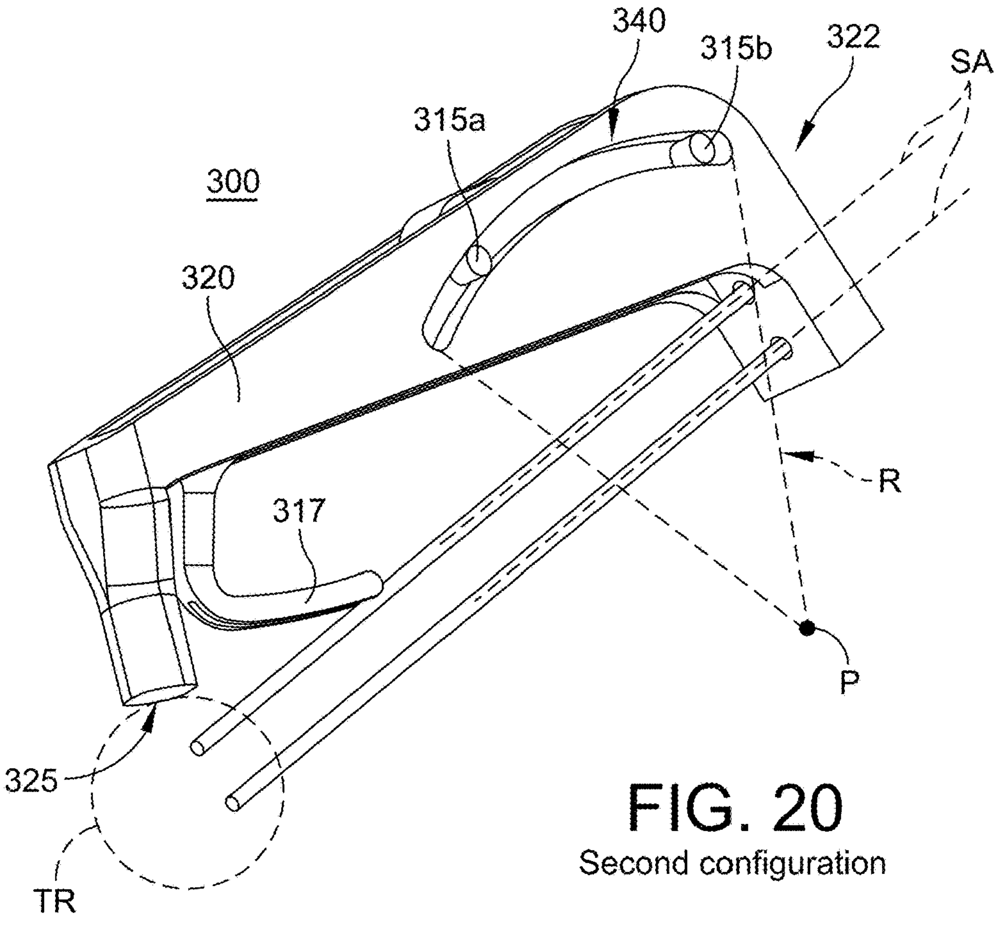

The first end 311 of the first portion 310 of the targeting guide 300 is configured for being inserted into an intramedullary canal of the first bone portion B1. Specifically, the first end 311 is configured as a hook-like structure that comprises a tip 317 that points back toward the second end 322 of the second portion 320. The first portion 310 and the second portion 320 are pivotally engaged to each other whereby the targeting guide can switch between a first configuration (open) and a second configuration (closed) by pivoting relative to each other. The first configuration is shown in FIG. 19. The second configuration is shown in FIG. 20.

The first end 321 of the second portion 320 comprises a bone contacting surface 325 for contacting and pushing the second bone portion B2 off-axis relative to the first bone portion B1 while the tip 317 of the first end 311 of the first portion 310 is inserted into the intramedullary canal of the first bone portion B1. Effectively, the tip 317 of the first portion 310 is the anchor that anchors the targeting guide 300 in place with respect to the first bone portion B1 as the targeting guide 300 is moved from its first configuration (i.e., open) to the second configuration (see FIGS. 19 and 20).

Figure 22:
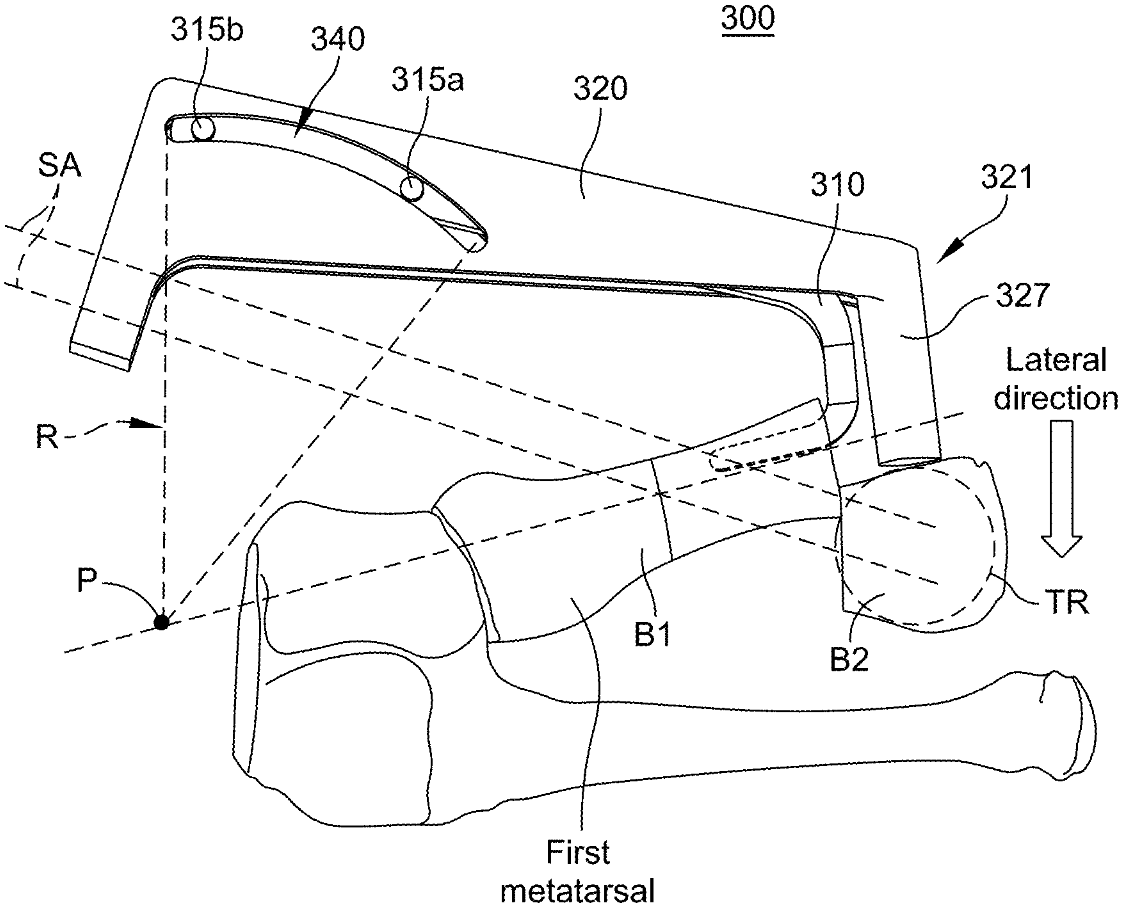

The tip 317 of the first end 311, provides the initial translation of the second bone portion B2 as the tip 317 is inserted into the intramedullary canal of the first bone portion B1, because the second bone portion B2 necessarily has to be pushed aside to access the intramedullary canal of B1. Then, by subsequently manipulating the targeting guide 300 into its second configuration (i.e., closed) (see FIG. 20) by closing the first portion 310 and the second portion 320 together, the first end 321 of the second portion 320 pushes on the second bone portion B2 and translates the second bone portion B2 into the final desired position. In the surgical procedure for correcting hallux valgus deformity, the second bone portion B2 of a first metatarsal bone is preferably translated in the lateral direction. This lateral translation direction is noted by an arrow in FIG. 22.

The second end 322 of the second portion 320 is provided with at least one guide hole 323 extending through the second end 322, whereby the at least one guide hole 323 are oriented such that the at least one guide hole's longitudinal axis SA are aimed toward a target region TR defined in proximity of the bone contacting surface 325 of the first end 321. This is illustrated in FIG. 20.

In some embodiments of the targeting guide 300, the at least one guide hole 323 is sized and configured to receive a guide sleeve or a guide wire therethrough.

In some embodiments of the targeting guide 300, the second end 322 of the second portion 320 is provided with at least two guide holes 323 extending through the second end 322, where the two guide holes 323 are oriented parallel to each other and the two guide holes' longitudinal axes SA are aimed toward the target region TR.

In some embodiments of the targeting guide, the bone contacting surface 325 is a substantially flat surface. In some embodiments, the bone contacting surface 325 has a notch 325*a* for contacting the distal bone fragment B2. An example of the notched bone contacting surface 325*a* is illustrated in the embodiments shown in FIGS. 23 and 24A-24C.

The target region TR is defined to have substantially the size of the distal fragment of the first metatarsal bone and the target region tangentially contacts the first end of the second part.

Figure 21:
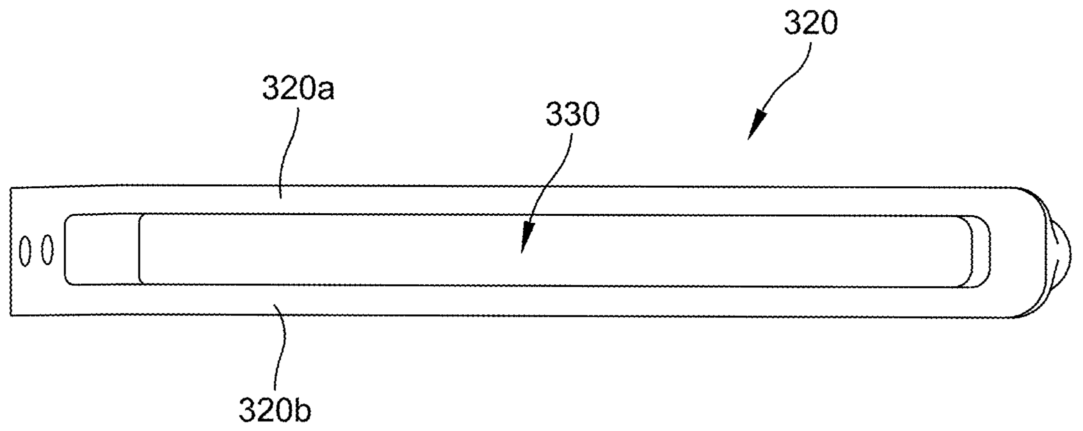

As shown in FIG. 21, the second portion 320 comprises an opening 330 provided in between the first and second sides 320*a*, 320*b* of the second portion 320 and also between the first end 321 and the second end 322. The second end 312 of the first portion 310 extends into the opening 330 and pivotally engage the second portion 320. The pivotal engagement is achieved by a pair of curved slots 340 provided on the second portion 320: one on each of the two sides 320*a*, 320*b*, and two guide pins 315*a*, 315*b* provided on the first portion 310.

The two guide pins 315*a*, 315*b* are provided to be spaced apart within the curved slots 340. The two guide pins 315*a*, 315*b* extend through the first portion 310 and extend into the curved slots 340 on both sides of the device. For purposes of discussion, the guide pin that is located closer to the first end 311 of the first portion 310 and labeled as 315*a* will be referred to as the first guide pin and the guide pin that is located closer to the second end 312 of the first portion 310 and labeled as 315*b* will be referred to as the second guide pin.

The curved slots 340 are longer than the distance between the two guide pins 315*a*, 315*b*. The first portion 310 and the second portion 320 pivot with respect to each other about a pivot axis P shown in FIG. 20. The curvature of the curved slots 340 are defined by a radius of curvature R measured from the pivot axis P. This configuration allows the first portion 310 and the second portion 320 to pivot about the pivot axis P as shown in FIG. 20. This results in a pivoting movement of the first portion 310 and the second portion

Figure 23:
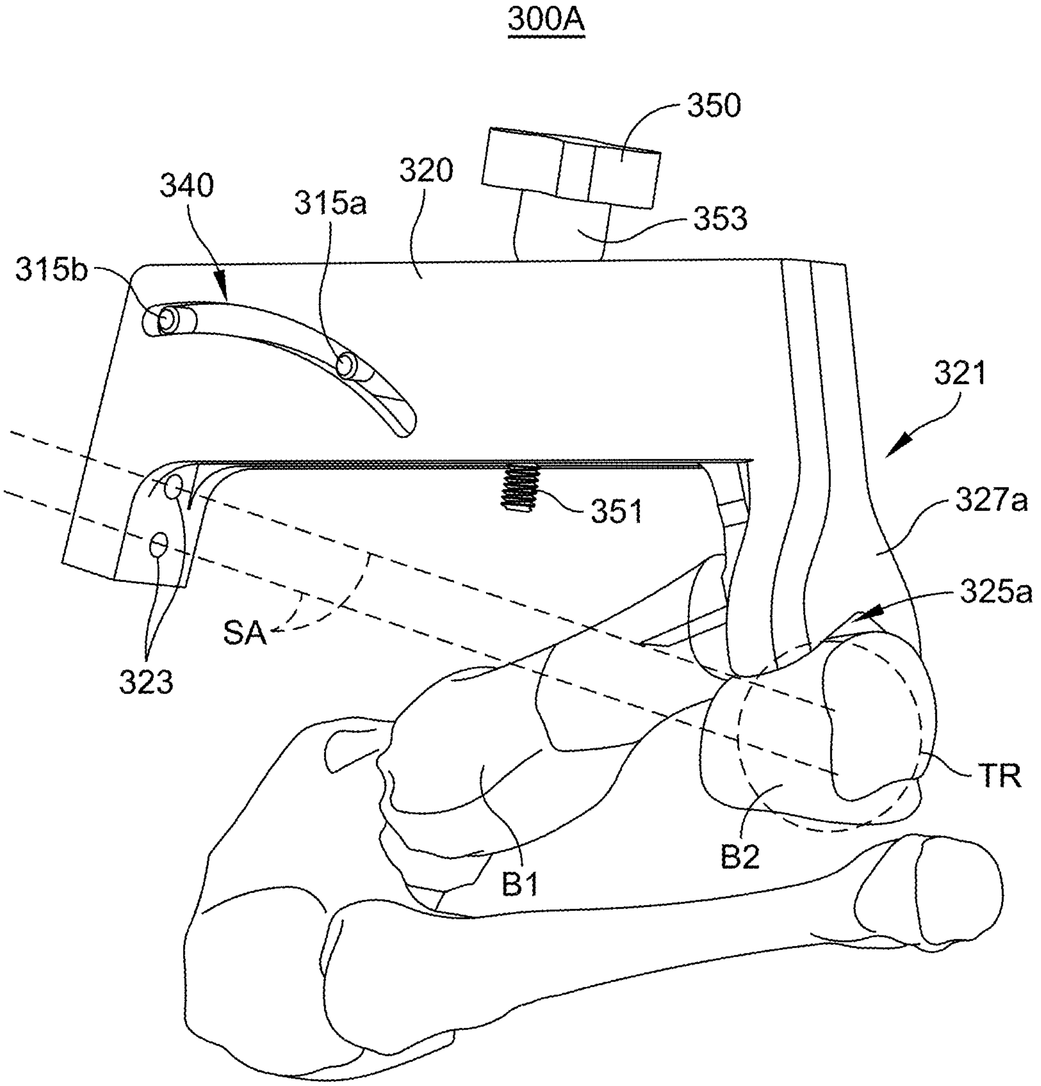
FIGS. 23-24C are illustrations of targeting guides according to other embodiments.

320 with respect to each other about the pivot axis P between the first configuration shown in FIG. 19 and the second configuration shown in FIG. 20. Preferably, the pivot axis P intersects with the longitudinal axis of the first bone portion B1 (i.e. the first metatarsal) as shown in FIG. 23. With this configuration, as the distal bone piece, the second bone portion B2, is corrected by laterally being translated, it's correction follows a path that mimics an angular realignment of the entire first bone away from its pathological varus position.

In the first configuration shown in FIG. 19, the second portion 320 is pivoted all the way back towards the second end 312 of the first portion 310 so that the first guide pin 315*a* is all the way at the end of the curved slots 340 that is closer to the first end 321 of the second portion 320. In the second configuration shown in FIG. 20, the second portion 320 is pivoted in the opposite direction all the way forward towards the first end 311 of the first portion 310 so that now the second guide pin 315*b* is all the way at the end of the curved slots 340 that is closer to the second end 322 of the second portion 320.

The interaction between the guide pins 315*a* and 315*b* and the curvature of the curved slots 340 produce the pivoting motion between the first portion 310 and the second portion 320 such that as the targeting guide 300 goes from the first configuration to the second configuration, the bone contacting surface 325 on the second portion 320 moves downward with respect to the tip 317 of the first portion 310. Because of the pivoting motion between the first portion 310 and the second portion 320, the downward movement of the bone contacting surface 325 is in an arc which matches the curvature of the curved slots 340.

FIG. 23 is an illustration of a targeting guide 300A according to another embodiment. In this embodiment, the bone contacting surface 325*a* is notched rather than being flat to provide more secure engagement of the bone contacting surface 325*a* with the bone portion B2. The notched contacting surface 325*a* keeps the second bone portion B2 centered in the notch and can prevent the bone contacting surface 325*a* from slipping in dorsal-plantar directions. In preferred embodiments, the notch can be V-shaped or U-shaped.

The targeting guide embodiment 300A also includes an actuation mechanism 350 that allows the targeting guide's transition from its first configuration to the second configuration to be controlled gradually by the use of the actuation mechanism 350. The actuation mechanism 350 is inserted through the opening 330 in the second portion 320 from the top side and comprises a threaded stem 351 that threadedly engage the first portion 310 via a threaded hole (not visible) provided in the first portion 310. The head portion 353 of the actuation mechanism is wider than the opening 330 between the two sides 320*a*, 320*b* of the second portion 320 so that by turning the head portion 353, the threaded engagement between the actuation mechanism and the first portion 310 can raise the first portion 310 within the opening 330. Thus, the actuation mechanism 350 can be used to transition the targeting guide 300 from its first configuration to the second configuration.

Figure 24A:
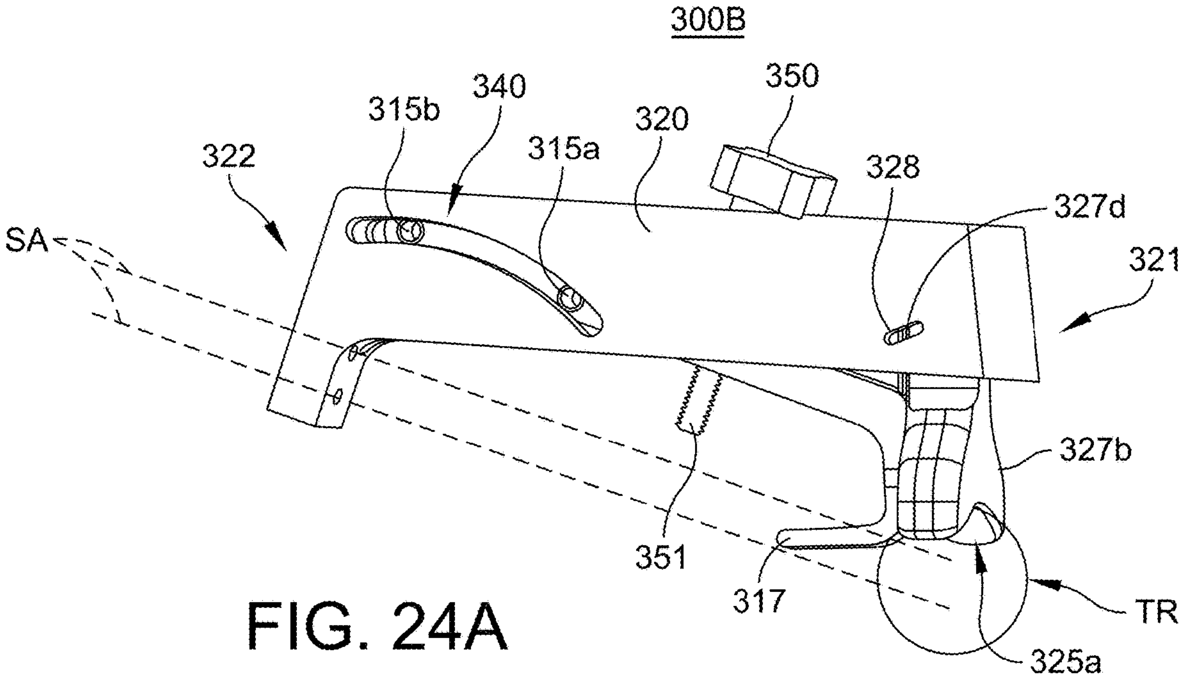
Figure 24B:
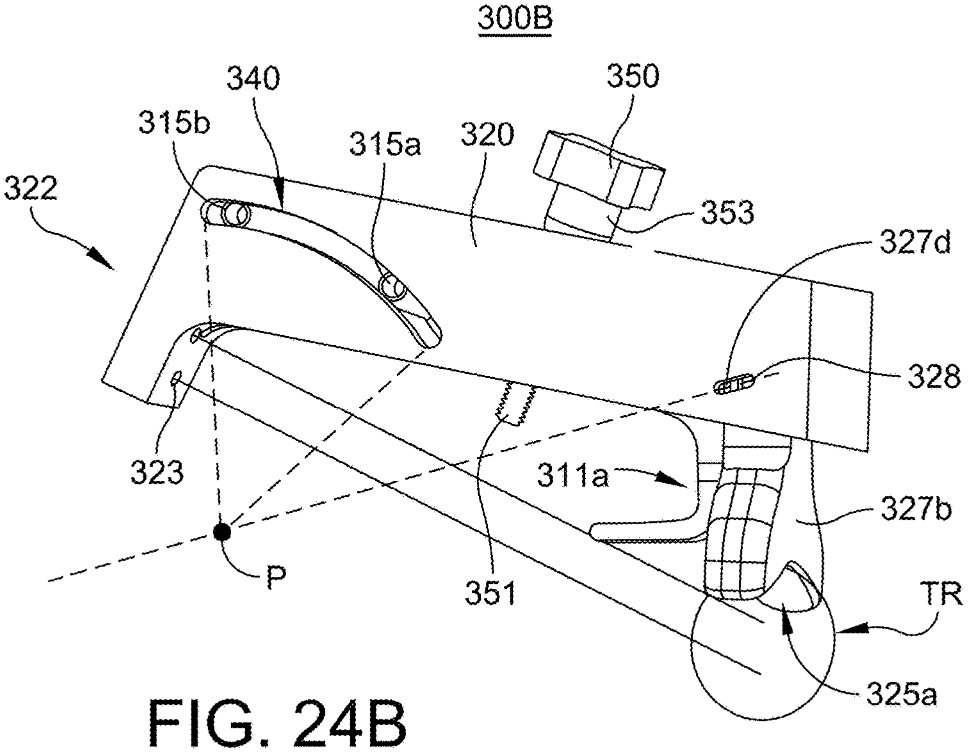
Figure 24C:
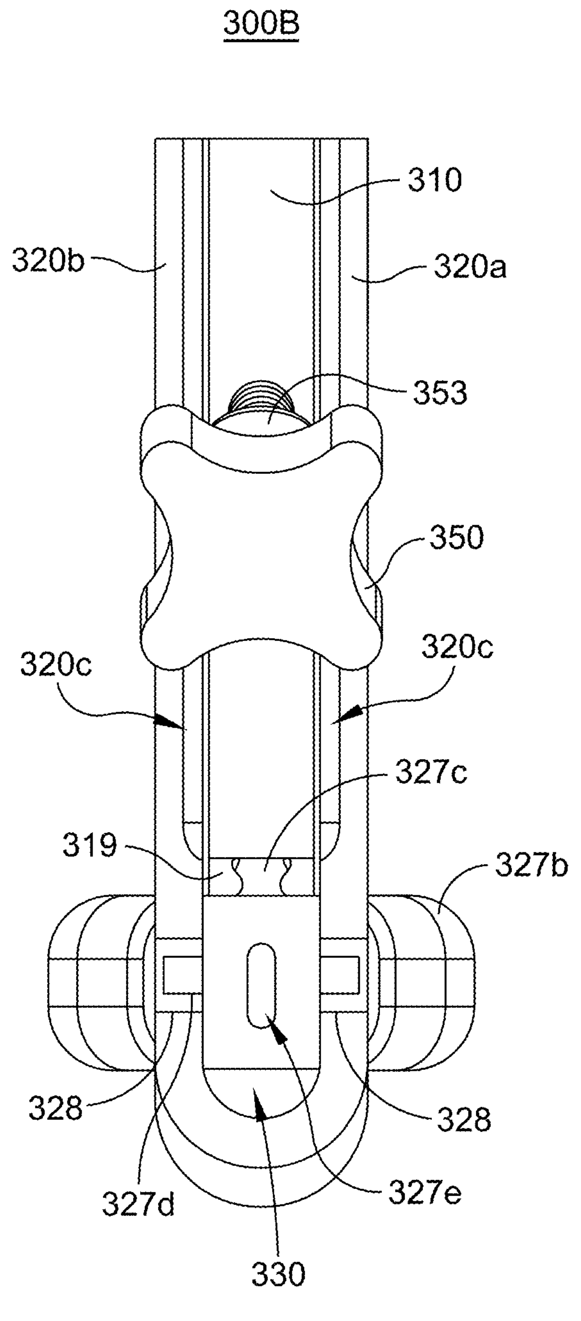

FIGS. 24A-24C are illustrations of a targeting guide 300B according to another embodiment. In this embodiment, the first end 321 of the second portion 320 is configured with a separate bone pushing piece 327 and the bone contacting surface 325*a* is provided on the bone pushing piece 327. In this embodiment, because the bone pushing piece 327 is a separate structure from the second portion 320 rather than being integrally formed with the second portion 320, the targeting guide 300B is more adaptable to variability in the shape and contour of the second bone portion B2. The bone pushing piece 327 slidably engages the first end 311 of the first portion 310 so that as the targeting guide 300B transitions from the first configuration (shown in FIG. 24A) to the second configuration (shown in FIG. 24B) the second portion 320 pushes on the bone pushing piece 327 which will slide downward along the straight portion 311*a* in the first end 311 of the first portion 310. Therefore, unlike in the targeting guide embodiments 300A and 300B, in which their bone pushing portions 327 and 327*a* move in an arc following the pivoting movement of the second portion 320 with respect to the first portion 310, in the targeting guide embodiment 300B, the bone pushing piece 327*b* moves in a linear sliding motion while the second portion 320 still moves in an arc.

In order to enable the linear sliding motion of the bone pushing piece 327*b*, the bone pushing piece 327*b* and the first end 311 of the first portion 310 are configured to engage each other via a sliding track arrangement. In the illustrated example, the first end 311 of the first portion 310 is configured with a pair of tracks 319 and the bone pushing piece 327*b* is configured with a center guide 327*c*. This arrangement can be seen in the top-down view shown in FIG. 24C. As can be seen in FIG. 24C, in some embodiments, the bone pushing piece 327*b* can be provided with a slot or an opening 327*e* extending through the bone pushing piece 327*b* to allow an additional anchoring wire to be thrown through the bone pushing piece 327*b* and into the second bone portion B2 if desired.

Additionally, in order to accommodate the arcuate motion of the second portion 320 and the linear motion of the bone pushing piece 327*b* at the same time, the first end 321 of the second portion 320 and the bone pushing piece 327*b* are configured to engage each other via a slot and pin arrangement. In the illustrated example, the second portion 320 is configured with a pair of slots 328, one on each of the sides 320*a*, 320*b* of the second portion 320, and the bone pushing piece 327*b* is configured with a pin 327*c* that extends from the slot 328 on one side 320*a* to the other side 320*b*. As shown in FIG. 24B, the slots 328 are oriented to intersect the pivot axis P such that the linear translation of the bone contacting surface 325*a* moves in lock-step with the pivoting action.

The targeting guide 300B is also illustrated with the actuation mechanism 350 described above in connection with the targeting guide embodiment 300A of FIG. 23. In the top-down view of FIG. 24C one can see chamfered surfaces 320*c* along the inner edge of the two sides 320*a*, 320*b* that accommodates the head portion 353 of the actuation mechanism 350.

Figure 25:
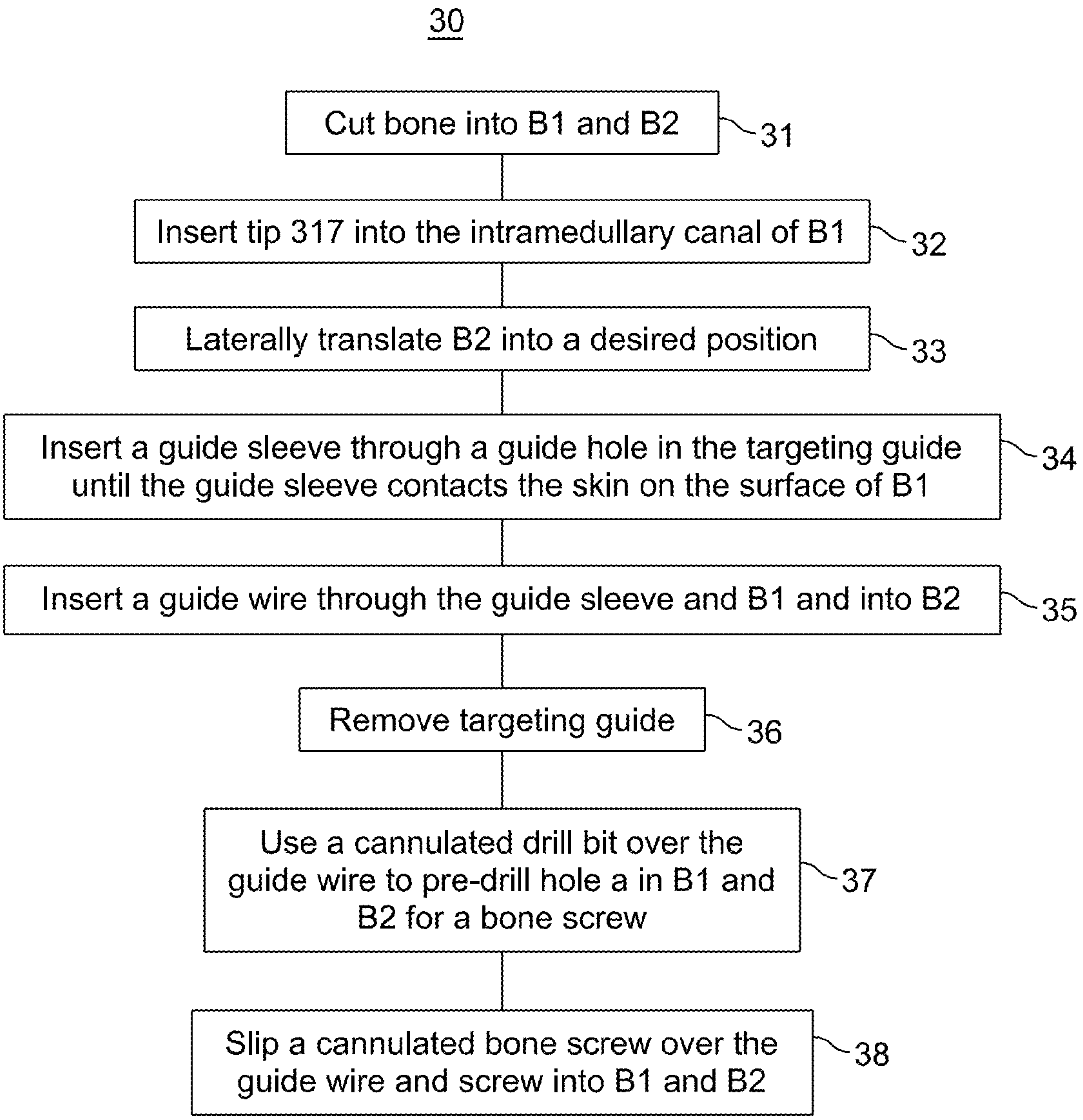
FIG. 25 is a flowchart illustrating a method of using some embodiments of a targeting guide of the present disclosure.

Referring to the flow chart 30 shown in FIG. 25, a method of using the targeting guides 300, 300A, 300B is disclosed. The method comprises an osteotomy cutting a bone into the first B1 and second B2 portions. (See Step 31). This can be a chevron osteotomy or a transverse osteotomy conducted as a minimally invasive procedure through a small (3-5 mm) percutaneous incision. In the illustrated example the bone is a first metatarsal bone and the procedure is for treating hallux valgus deformity in MTP (metatarsophalangeal) joint. Next, the tip 317 of the first end 311 of the first portion 310 is inserted into the intramedullary canal of the first portion B1 of the bone with the targeting guide 300 in the first configuration shown in FIG. 19. (See Step 32). In this configuration, the bone contacting surface 325 of the first end 321 of the second portion 320 is in contact with the second portion B2 of the bone. Next, the second portion B2 of the bone is laterally translated into a desired position by placing the targeting guide 300 into its second configuration. (See Step 33). Next, at least one guide sleeve SL is inserted through the at least one guide hole 323 in the second part 320 until the guide sleeve SL contacts the bone at a desired location on the surface of the first bone portion B1 of the metatarsal bone. (See Step 34). At this point, the guide sleeve SL defines a channel that will guide a guide wire G1 or a drill bit. Because the at least one guide hole 323 is oriented with its longitudinal axis SA oriented toward the target region TR, the guide sleeve SL and the channel defined by the guide sleeve SL are also oriented toward the target region TR. Next, a guide wire is inserted through the guide sleeve SL from the end of the guide sleeve SL at the guide hole 323 and advanced into and through the first portion B1 and into the second portion B2 of the bone which will be positioned in the target region TR. (See Step 35). The trajectory of the guide sleeve SL is shown by the longitudinal axes SA illustrated in FIGS. 20 and 23. The guide wire penetrates into the second bone portion B2 but does not go all the way through the second bone portion B2. Next, the targeting guide 300 is removed. (See Step 36). At this point, the use of the targeting guide 300 is completed. Next, a cannulated drill bit is used over the guide wire to pre-drill a hole through B1 and into B2 for a bone screw. (See Step 37). Next, a cannulated bone screw is slipped over the guide wire and screwed into and through the first bone portion B1 and into the second bone portion B2, thus securing the two bone portions B1 and B2 in their new positions. (See Step 38). The secured positions of the bone portions B1 and B2 is shown in FIG. 26.

Figure 27A:
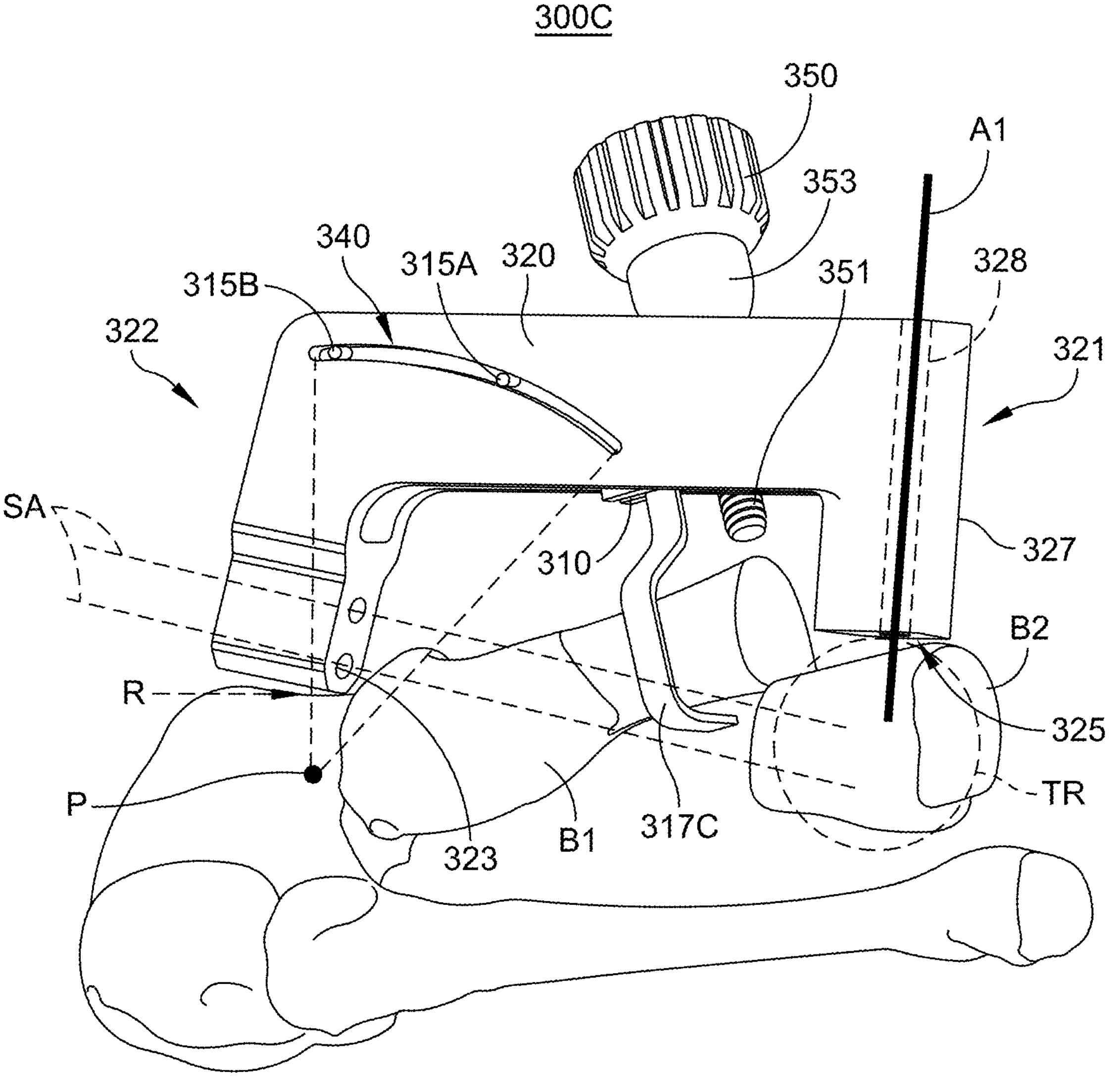
FIGS. 27A-27B are illustrations showing another embodiment of a targeting guide.

Shown in FIG. 27A is a targeting guide 300C that is a variation on the targeting guide embodiments 300, 300A, and 300B. As with the targeting guide 300, the targeting guide 300C comprises a first portion 310 and a second portion 320 that are pivotally engaged to each other by operation of the interaction between guide pins 315*a* and 315*b* and curved slots 340 about a pivot axis P. As with the targeting guide embodiments 300, 300A, and 300B, the targeting guide 300C can switch between a first configuration and a second configuration by pivoting relative to each other about the pivot point P.

Similar to the targeting guide embodiments 300A and 300B, the targeting guide embodiment 300C also includes an actuation mechanism 350 that allows the targeting guide's transition from its first configuration to the second configuration to be controlled by the use of the actuation mechanism 350. The actuation mechanism 350 extends through an opening 330 in the second portion 320 from the top side and comprises a threaded stem 351 that threadedly engages the first portion 310 via a threaded hole 310*a* provided in the first portion 310. The structure of the first portion 310 can be seen in the exploded view of the targeting guide 300C in FIG. 27B.

The second portion 320 comprises a first end 321 and a second end 322. The first end 321 comprises a bone pushing piece 327 which comprises a bone contacting surface 325 for contacting and pushing the second bone portion B2 off-axis relative to the first bone portion B1 as the targeting guide 300C transitions from its first configuration to the second configuration. During the transition from the first configuration to the second configuration, the tip 317 of the first end 311 of the first portion 310 pulls on the first bone portion B1 in the direction opposite from the direction the bone pushing piece 327 urges the second bone portion B2.

Rather than the tip 317 for inserting into the intramedullary canal of the first bone portion B1 provided at the first end 311 of the first portion 310 of the targeting guide embodiment 300, the first portion 310 of the targeting guide 300C comprises a curved U-shaped hook-like tip 317C that is open to the plantar direction when targeting guide 300C is positioned next to a patient's foot on the medial side of the foot in the orientation shown in FIG. 27A. The bone pushing piece 327 comprises a bone contacting surface 325 and a hole 328 extending through the whole length of the bone pushing piece 327.

FIG. 27A shows the targeting guide 300C in its second configuration, i.e., the configuration where the targeting guide has laterally translated the second bone portion B2 (the metatarsal head fragment) with respect to the first bone portion B1 (the metatarsal shaft fragment). As with the targeting guide embodiment 300, the targeting guide 300C is configured to be moved between the second configuration and a first configuration. The first configuration is the base configuration of the instrument that is used to make the initial engagement with the first metatarsal of the patient after the metatarsal has been cut into the two bone portions B1 and B2. The second configuration, the targeting guide has laterally translated the second bone portion B2 with respect to the metatarsal shaft fragment B1.

Figure 27B:
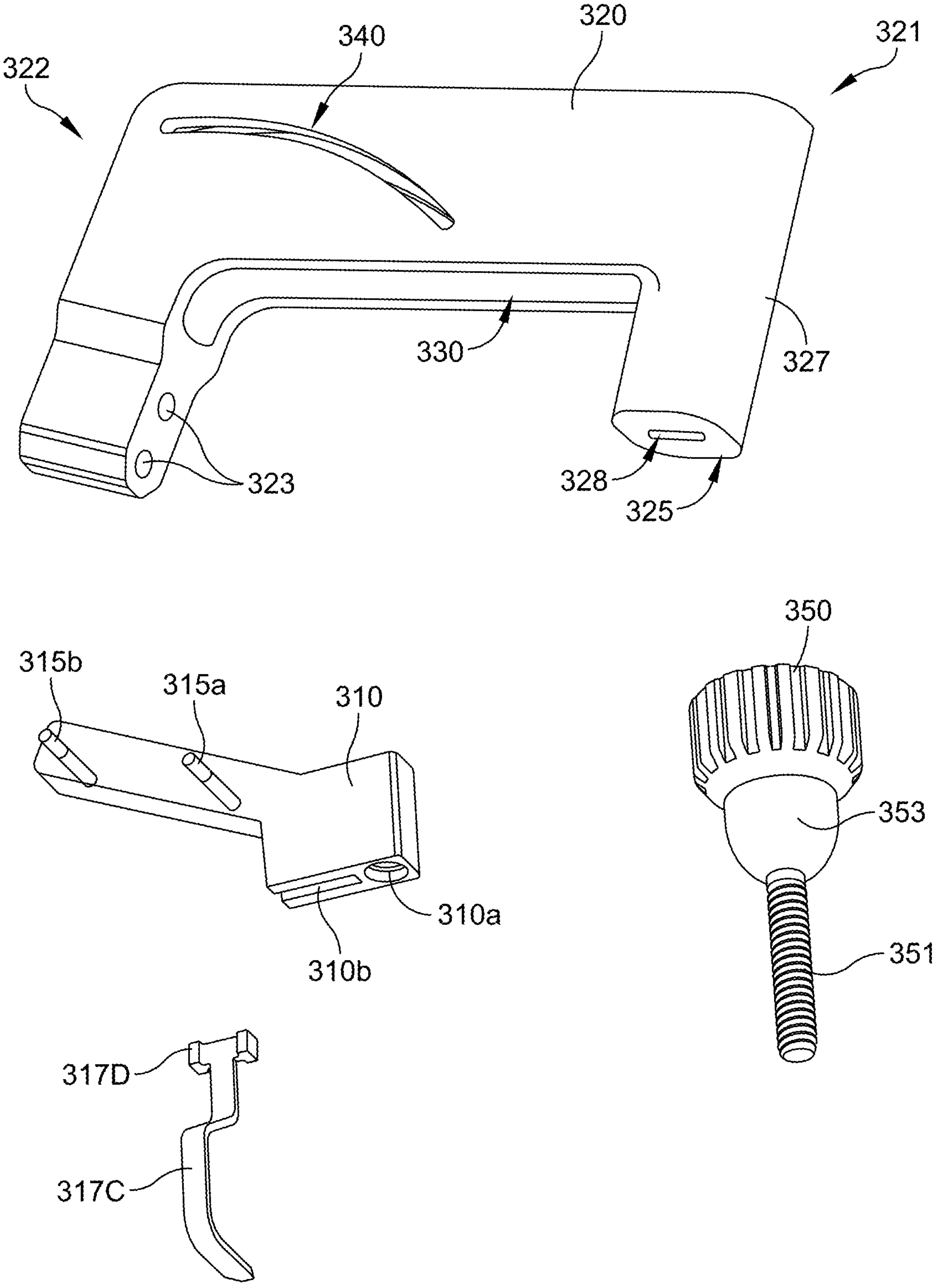

FIG. 27B shows an exploded view of the components of the targeting guide 300C. The second portion 320 comprises a first end 321 and a second end 322. The first end 321 comprises a bone pushing piece 327 having a bone contacting surface 325. A hole 328 is provided in the bone contacting surface 325 extending through the length of the bone pushing piece 327 so that an anchoring element such as a K-wire can be inserted through the bone pushing piece 327 and exit through the bone contacting surface 325. At the second end 322 of the second portion 320 is provided one or more guide holes 323 for receiving guide elements or guiding sleeves.

Figure 27C:
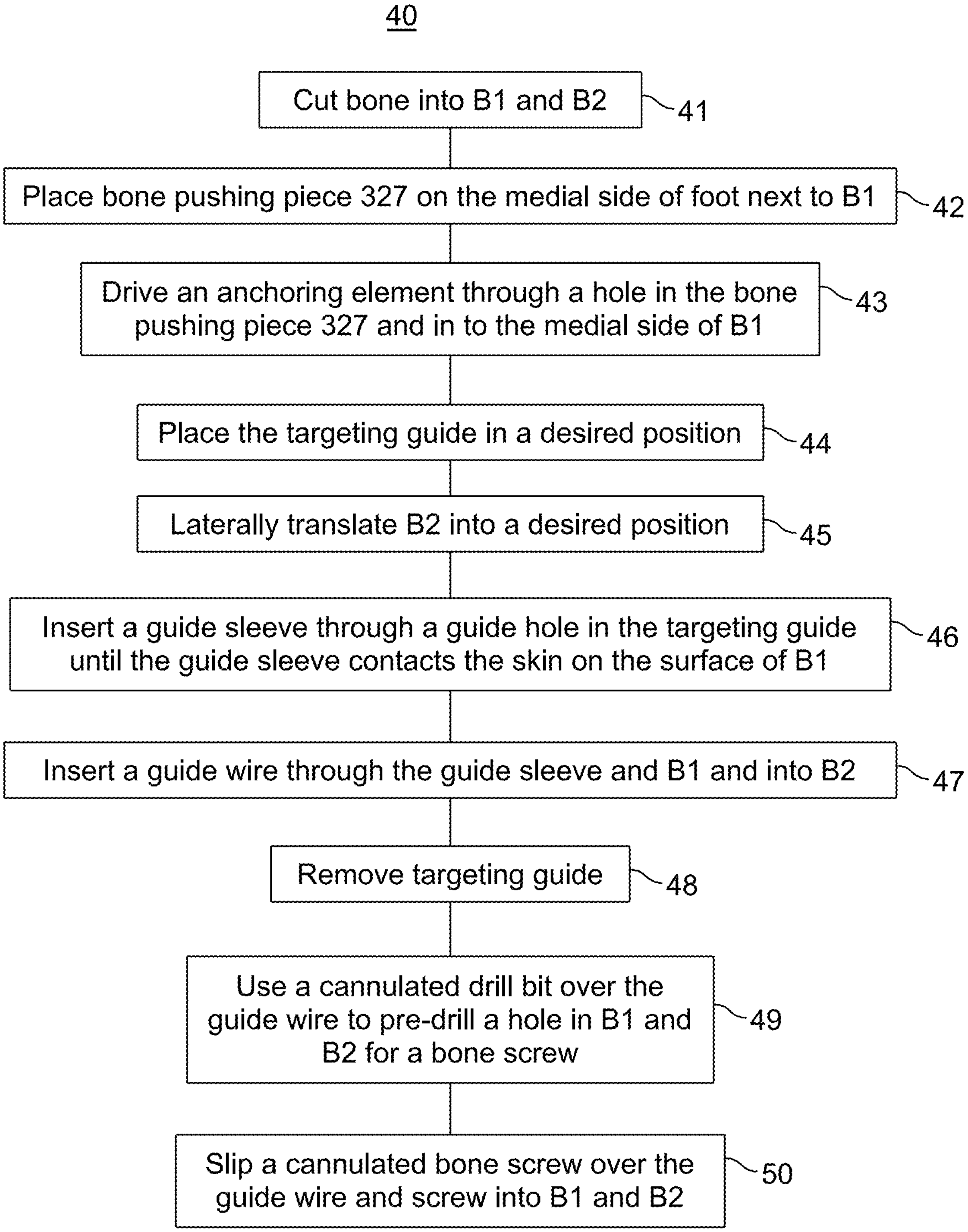
FIG. 27C is a flowchart illustrating a method of using the targeting guide embodiment shown in FIGS. 27A-27B.

Referring to the flow chart 40 shown in FIG. 27C, a method of using the targeting guide 300C is disclosed. The method comprises an osteotomy cutting a bone into the first B1 and second B2 portions. (See Step 41). This can be a chevron osteotomy or a transverse osteotomy conducted as a minimally invasive procedure through a small (3-5 mm) percutaneous incision. In the illustrated examples, the bone is a first metatarsal and the incision is made on the medial side of the metatarsal bone. The first bone portion B1 is the shaft fragment and the second bone portion B2 is the head fragment. Next, the bone pushing piece 327 of the targeting guide 300C is placed against the skin of the foot on the medial side of the second bone portion B2 with the bone contacting portion 325 contacting the skin. (See Step 42). Next, an anchoring element A1 such as a K-wire is inserted through the hole 328 in the bone pushing piece 327 and driven into the medial side of the second bone portion B2 through the bone contacting surface 325 as shown in FIG. 27A. (See Step 43). Then, the targeting guide 300C is rotated around the anchoring element A1 and positioned so that the U-shaped tip 317C cradles the first bone portion B1 from the dorsal side as shown in FIG. 27A. (See Step 44). The U-shaped tip 317C would need to be inserted through the medial incision and into the foot so that the U-shaped tip 317C can be positioned over the first bone portion B1 and cradling the bone. At this point, the targeting guide 300C is in its first configuration.

Next, the second bone portion B2 is laterally translated with respect to the first bone portion B1 by placing the targeting guide 300C into its second configuration. (See Step 45). As with the targeting guide embodiment 300A, this is accomplished by using the actuation mechanism 350. By turning the actuation mechanism 350 in the appropriate direction (the direction will depend on the handedness of the screw threads involved), the threaded engagement between the actuation mechanism 350 and the first portion 310 pulls on the first portion 310 causing it to pivot about the pivot point P by the operation of the guide pins 315*a*, 315*b* captured in the curved slots 340. As the first portion 310 is pulled in the medial direction with respect to the second portion 320, the U-shaped tip 317C cradling pulls the metatarsal shaft fragment B1 in the medial direction and at the same time the bone pushing piece 327 of the second portion 320 pushes against the second bone portion B2 in the lateral direction. Once a desired amount of lateral translation of the metatarsal head fragment B2 is achieved, at least one guide sleeve SL is inserted through the at least one guide hole 323 in the second part 320 until the guide sleeve SL contacts the bone at a desired location on the surface of the first bone portion B1. (See Step 46). At this point, the guide sleeve SL defines a channel that will guide a guide wire G1 or a drill bit. Because the at least one guide hole 323 is oriented with its longitudinal axis SA oriented toward the target region TR, the guide sleeve SL and the channel defined by the guide sleeve SL are also oriented toward the target region TR. Next, a guide wire is inserted through the guide sleeve SL from the end of the guide sleeve SL at the guide hole 323 and advanced into and through the metatarsal shaft fragment B1 and into the metatarsal head fragment B2 which will be positioned in the target region TR. (See Step 47). The trajectory of the guide sleeve SL is shown by the longitudinal axes SA illustrated in FIG. 27B. The guide wire penetrates into the metatarsal head fragment B2 but does not go all the way through the head fragment B2. Next, the targeting guide 300C is removed. (See Step 48). At this point, the use of the targeting guide 300C is completed. Next, a cannulated drill bit is used over the guide wire to pre-drill a hole through B1 and into B2 for a bone screw. (See Step 49). Next, a cannulated bone screw is slipped over the guide wire and screwed into and through the two bone fragments B1 and B2, thus securing the two bone fragments B1 and B2 in their new positions. (See Step 50). The secured final positions of the bone fragments B1 and B2 is shown in FIG. 26.

In some embodiments, the U-shaped tip 317C is configured so that the U-shaped tip can reach over the first metatarsal bone and engage or cradle one of the other metatarsal bones. In order to enable this the U-shaped tip 317C is elongated so that the opening formed by the U-shape is sufficiently long to reach whichever is the intended metatarsal bone. Because the U-shaped tip 317C can be configured as a modular unit separate from the first portion 310 as shown in the exploded view in FIG. 27B, the targeting guide 300C can be provided in a surgical kit with a plurality of U-shaped tip 317C each having a different length. Having the option of using a longer U-shaped tip 317C that can engage the second or third metatarsal bone rather than the first metatarsal bone can be useful in some situations where hook-end of the U-shaped tip 317C may be in the way of the trajectories of the longitudinal axes SA into the target region TR.

Figure 29A:
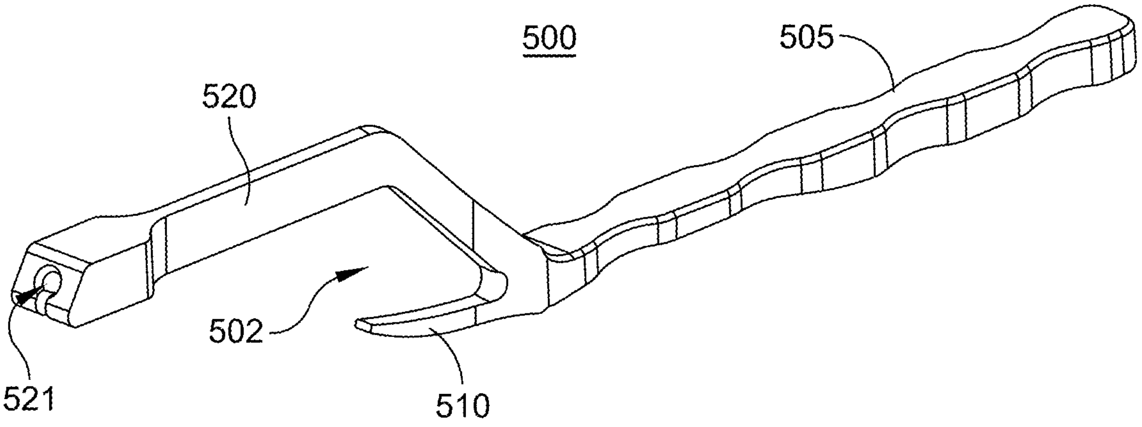
FIGS. 29A and 29B are illustrations showing another embodiment of a targeting guide.
Figure 29B:
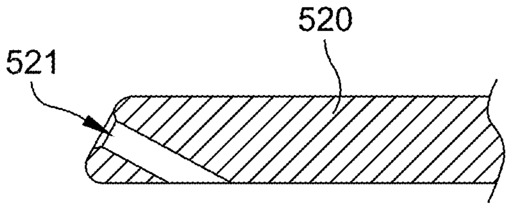

FIGS. 29A-32D show targeting guide embodiments 500, 500A, 500B, and 500C. The targeting guides 500, 500A, 500B, and 500C are useful for guiding the placement of bone screws through the two bone portions B1, B2 involved in the correction of hallux valgus defect. The targeting guide 500 comprises an elongated handle portion 505 and a bifurcated working end 502. The working end 502 comprises a translator part 510 and a guide part 520. The translator part 510 is a pointed extension that is intended to be inserted into the intramedullary canal of the cut end of the first bone portion B1 (the metatarsal shaft fragment). The guide part 520 extends in-line with the translator part 510, extends beyond the tip of the translator part 510. The guide part 520 comprises at least one guide hole 521 that is oriented for guiding one or more guiding element G1 that will guide the placement of a bone screw through the two bone portions B1, B2 when the translator part 510 is inserted into the intramedullary canal of the first bone portion B1. In the illustrated example in FIG. 29A, the distal end of the guide part 520 is shown with only one guide hole 521. However, the distal end of the guide part 520 can be configured to have more than one guide holes as appropriate. A guide sleeve SL1 can be inserted through the guide hole 521 and a guiding element G1 can be inserted through the guide sleeve. Alternatively, a guiding element G1 of an appropriate diameter can be inserted through the guide hole 521 directly without the use of a guide sleeve SL1. The longitudinal axis of the guide hole 521 defines a second axis SA as shown in FIG. 29A. Thus, when a guiding element G1 is placed through the guide hole 521 (whether directly or via a guide sleeve SL1), the guiding element G1 will be oriented along the second axis SA. The second axis SA represents the trajectory of the bone screw that is intended to be driven through the two bone portions B1, B2 guided by the guiding element G1.

FIGS. 30A-30F show a targeting guide 500A according to another embodiment. In this embodiment, a hinge joint 522 is located at a point along the length of the guide part 520 so that the distal end portion of the guide part 520 is a hinged part 520A. The hinged part 520A comprises at least one guide hole 521 that is oriented for guiding one or more guiding element G1 that will guide the placement of a bone screw through the two bone portions B1, B2 when the translator part 510 is inserted into the intramedullary canal of the first bone portion B1. The illustrated example only shows one guide hole 521 but the hinged part 520A can be configured to have more than one guide holes as appropriate. The hinged part 520A can be moved between the two positions shown in FIGS. 29A and 29B by its hinge action. Flipping the hinged part 520A up into the position shown in FIG. 29B temporarily shortens the working length of the guide part 520. In some situations, this can be useful for the surgeon in maneuvering the targeting guide 500 around the patient's foot.

Figure 30A:
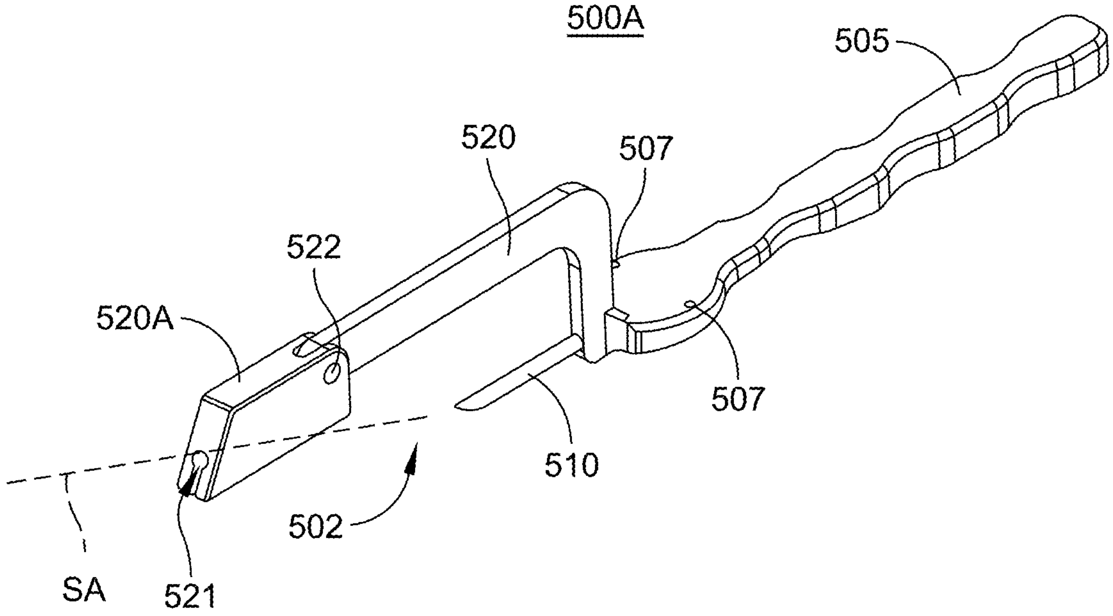
FIGS. 30A through 30F are illustrations showing another embodiment of a targeting guide.
Figure 30B:
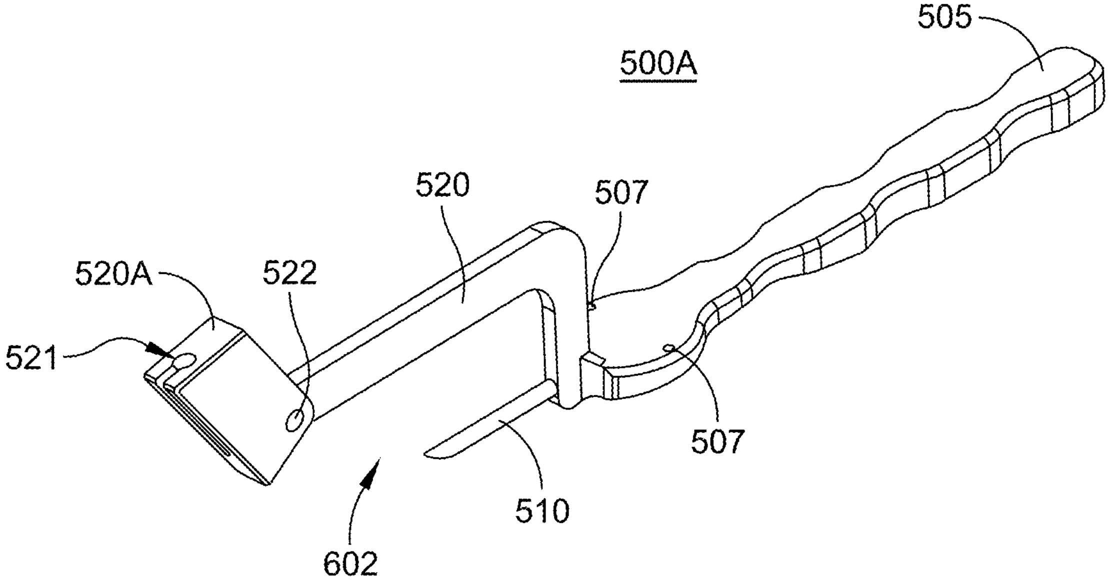
Figure 30C:
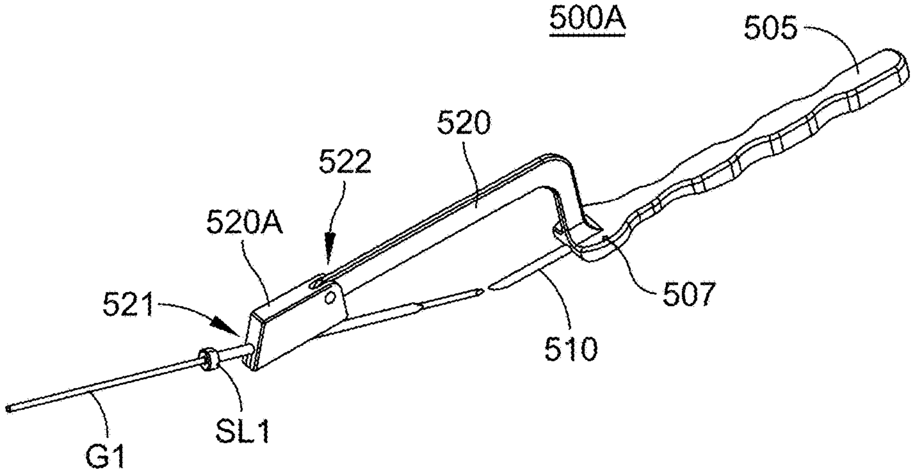
Figure 30D:
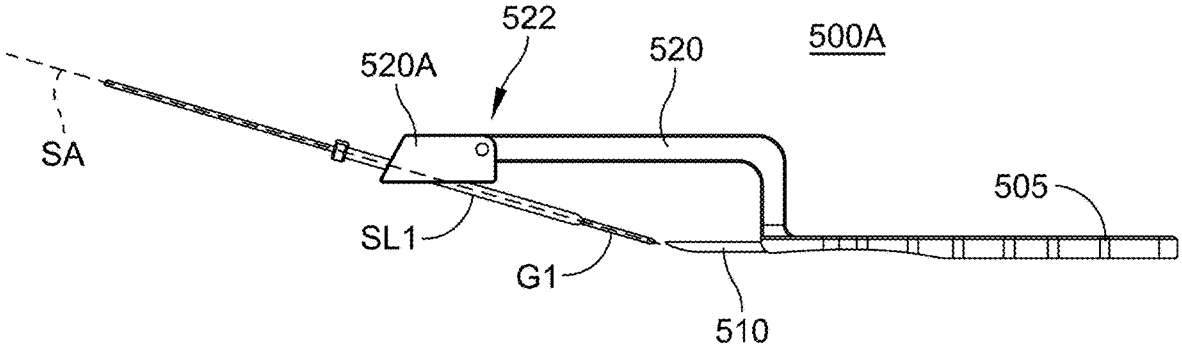

As shown in FIG. 30C, a guide sleeve SL1 can be inserted through the guide hole 521 and a guiding element G1 is inserted through the guide sleeve. Alternatively, a guiding element G1 of an appropriate diameter can be inserted through the guide hole 521 directly without the use of a guide sleeve SL1. The longitudinal axis of the guide hole 521 defines a second axis SA as shown in FIGS. 30A and 30D. Thus, when a guiding element G1 is placed through the guide hole 521 (whether directly or via a guide sleeve SL1), the guiding element G1 will be oriented along the second axis SA. The second axis SA represents the trajectory of the bone screw that is intended to be driven through the two bone portions B1, B2 guided by the guiding element G1.

Figure 30E:
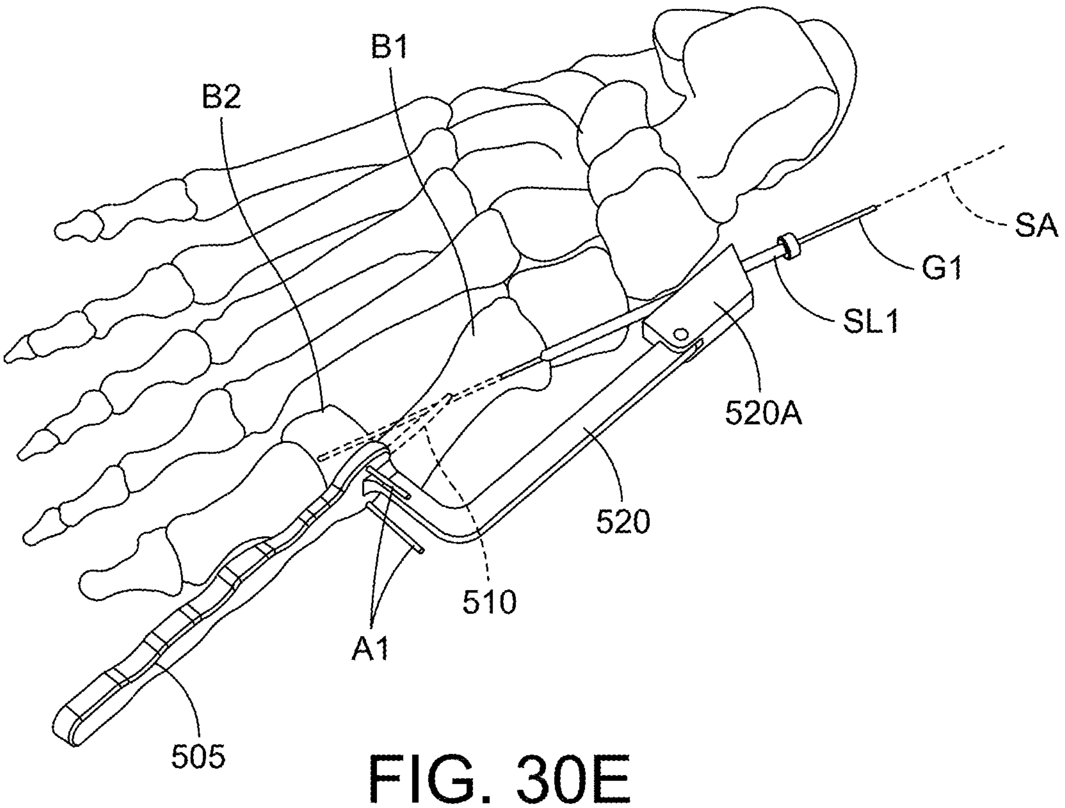

As shown in FIG. 30E, the guide part 520 extends to a length that is sufficient to position the guide hole 521 in the hinged part 520A further in the proximal direction beyond the proximal end of the first bone portion B1 (the metatarsal shaft) when the translator part 510 is fully inserted into the intramedullary canal of the first bone portion B1. In this position, with the hinged part 520A contacting the skin of the patient's foot, the second axis SA defined by the guide hole 521 represents the desired trajectory for the bone screw to be placed via the proximal end of the first bone portion B1, through the first bone portion B1 and into the second bone portion B2.

Figure 30F:
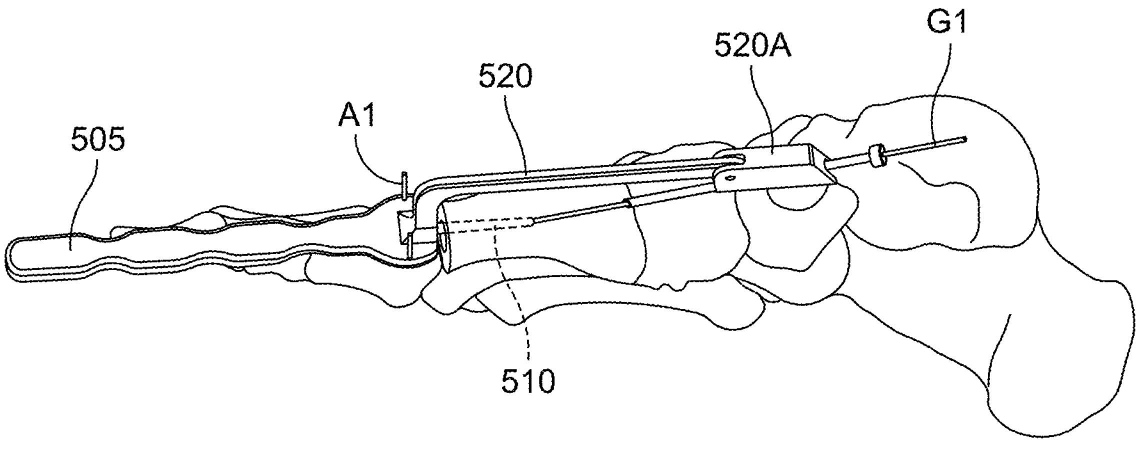

After an MIS osteotomy (can be a chevron osteotomy or a transverse osteotomy) is performed on a metatarsal bone and cut into two portions B1 and B2, the translator part 510 is inserted into the intramedullary canal of the first bone portion B1 (the shaft portion of the metatarsal). Then, using the translator part 510 as a fulcrum the surgeon can move the handle 505 in the medial-lateral direction to push and translate the second bone portion B2 (the head of the metatarsal) in lateral direction resulting in a configuration shown in FIG. 30E. With the two bone portions B1, B2 held in the desired translated configuration, a pair of anchoring elements A1, A2 can be inserted through holes 507 in the handle portion 505 to temporarily anchor the targeting guide to the second bone portion B2. Next, a guide sleeve SL1 is inserted through the guide hole 521 until the tip of the guide sleeve SL1 contacts the skin near the proximal end of the first bone portion B1. In this configuration, the relationship of the targeting guide 500A and the metatarsal bone portions B1, B2 will be as shown in FIG. 30E. FIG. 30F is an elevation view of the targeting guide 500A in this position. The second axis SA defined by the guide hole 521 and the guide sleeve SL1 represents the desired trajectory for the bone screw to be threaded into the two bone portions B1, B2 to affix the bone portions. Next, a guide element G1 is inserted into the guide sleeve SL1 and then driven through the two bone portions B1, B2, entering the proximal end of the first bone portion B1, through the first bone portion, and then into the second bone portion B2 following the trajectory defined by the second axis SA.

Once the guiding element G1 is in place, the targeting guide 500A can be removed. Next, a cannulated drill can be used over the guiding element G1 to pre-drill a hole through the two bone portions B1, B2. Then, a cannulated bone screw can be slipped over the guiding element G1 and threaded into the two bone portions B1, B2 and fixate them in their new configuration.

Figure 31A:
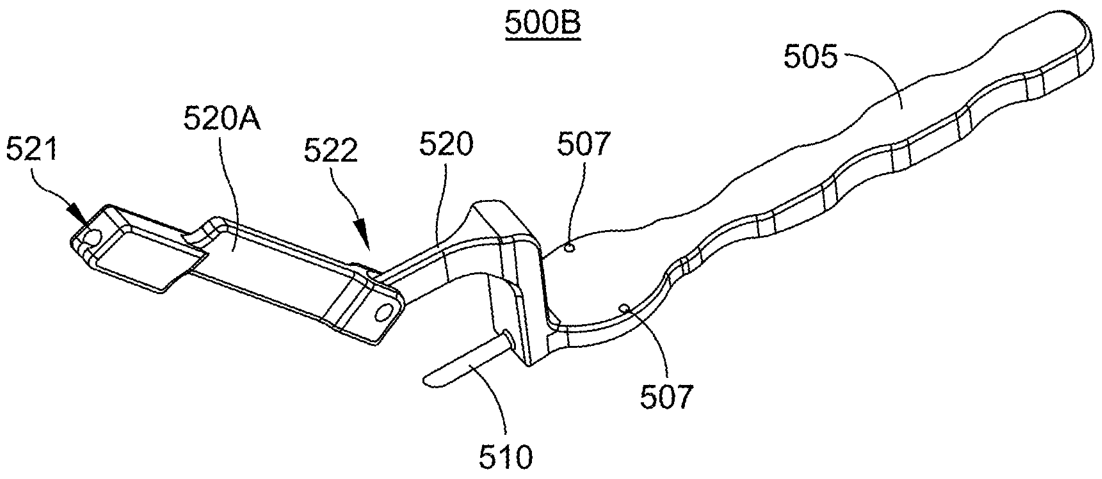
FIGS. 31A and 31B are illustrations showing another embodiment of a targeting guide.
Figure 31B:
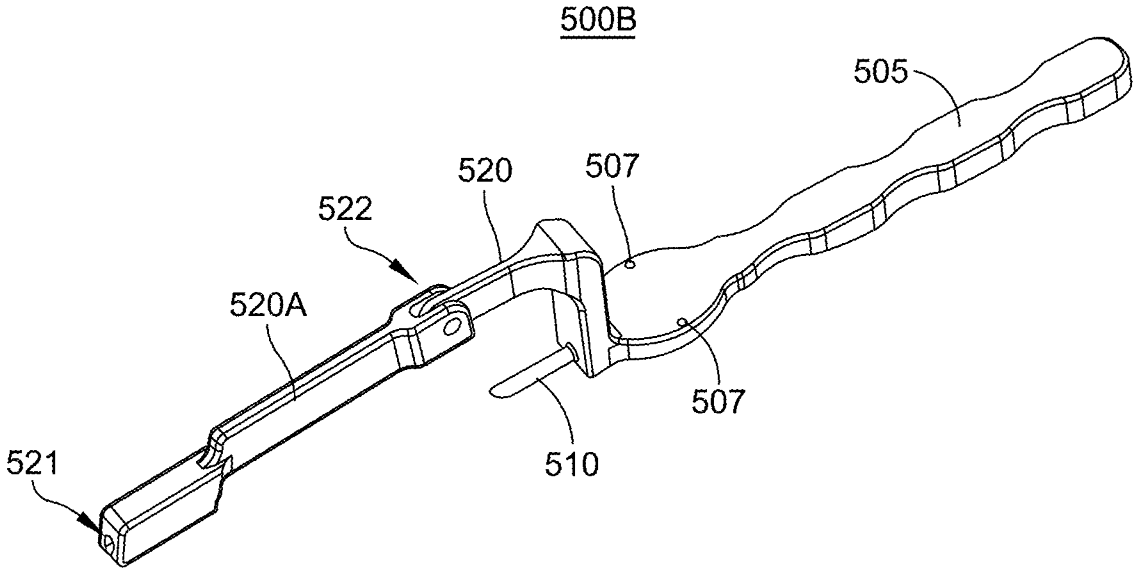
Figure 32A:
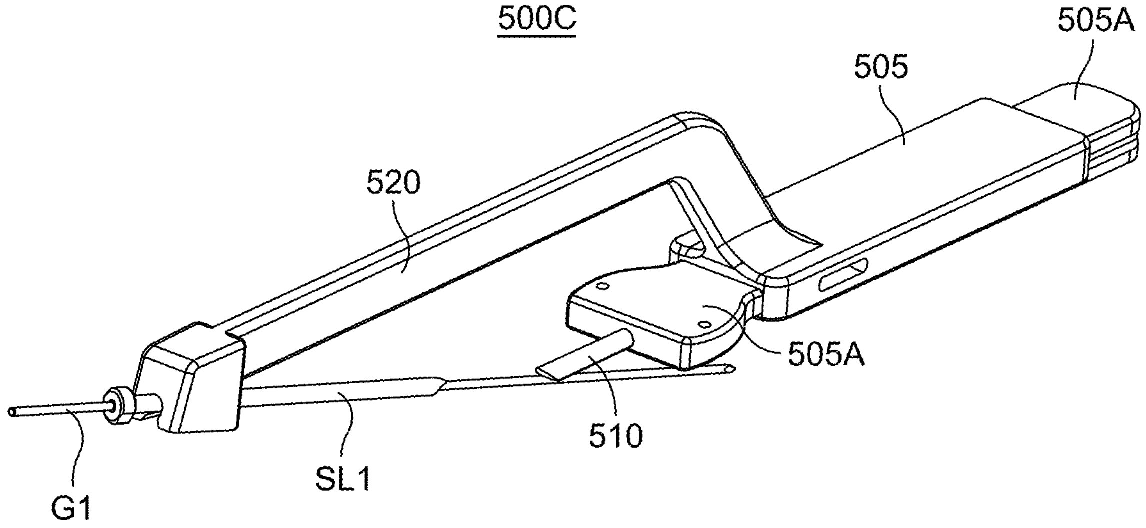
FIGS. 32A through 32D are illustrations showing another embodiment of a targeting guide.
Figure 32B:
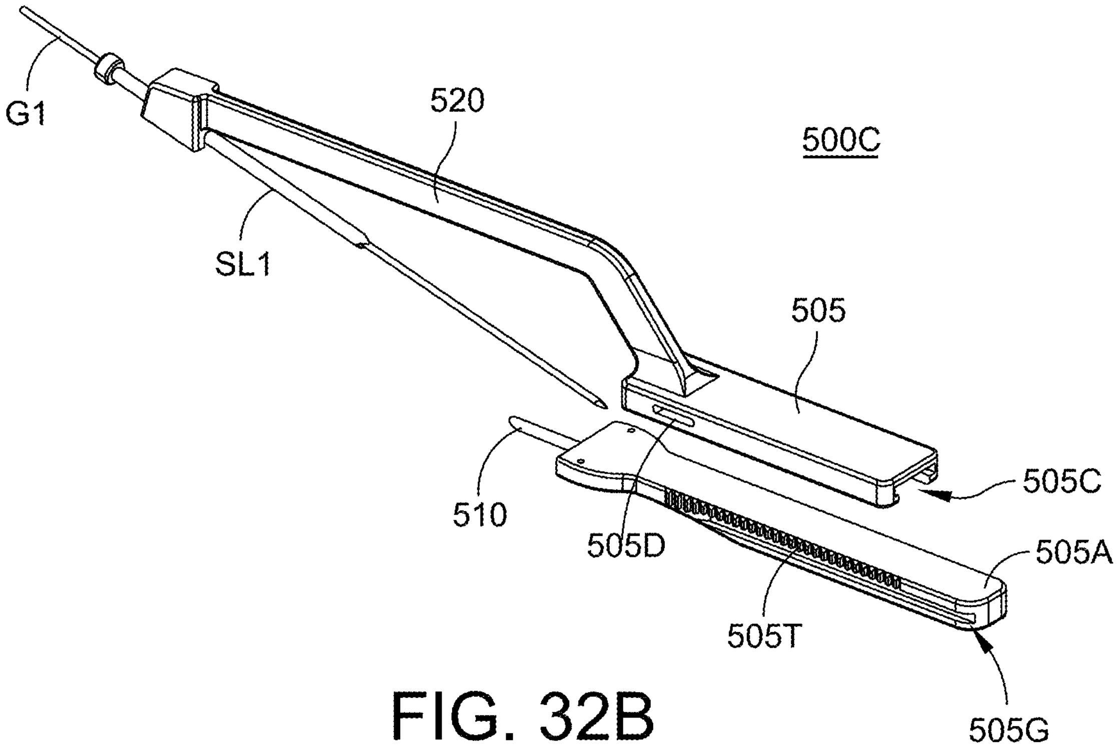
Figure 32C:
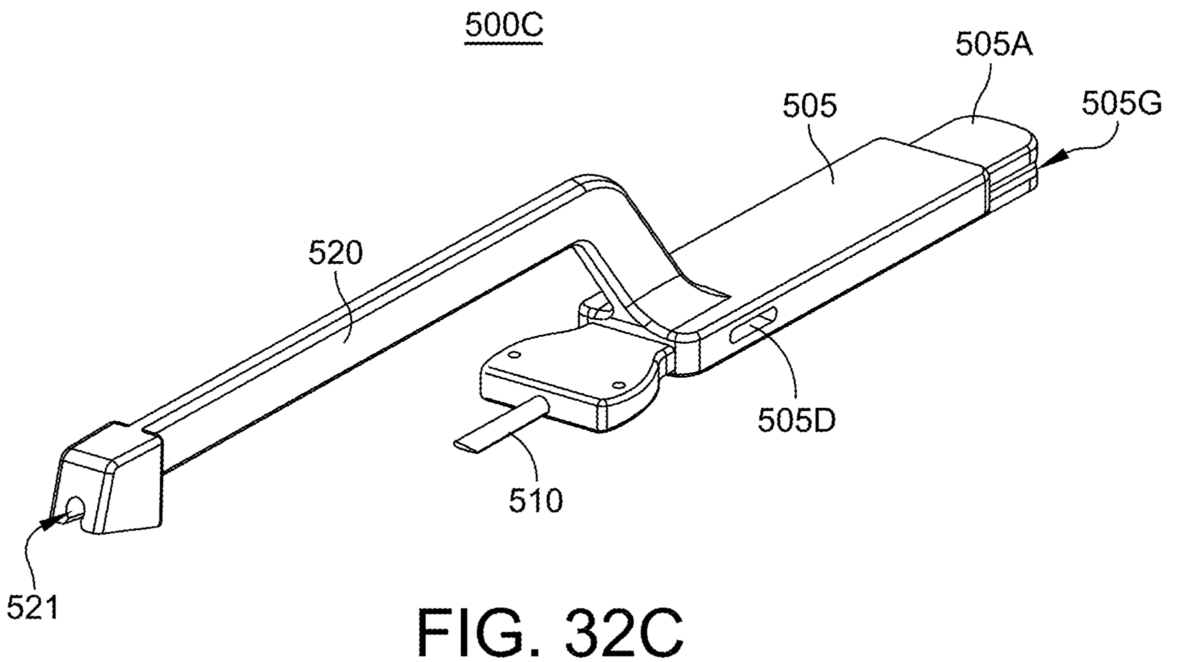
Figure 32D:
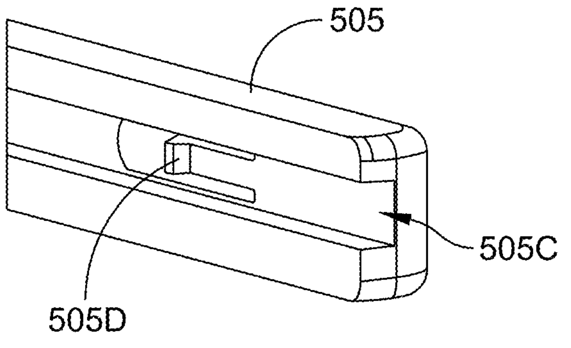

FIGS. 31A and 31B are illustrations of another embodiment of a targeting guide 500B which is a variation of the targeting guide 500. The targeting guide 500B also has a hinged part 520A at the end of which is provided at least one guide hole 521 for receiving a guide sleeve SL1 and/or a guiding element G1. As with the targeting guide 500A, the hinged part 520A can be configured to have more than one guide holes as appropriate. The location of the guide hole 521 with respect to the translator part 510 is the same or similar to that in the targeting guide 500. However, in the targeting guide 500B, the location of the hinged joint 522 is closer to the translator part 510. Having the hinged joint 522 closer to the translator port 510 makes the guide portion 520 to be shorter when the hinged part 520A is flipped up. This may be more useful depending on the circumstances around the patient's foot during the surgical procedure.

FIGS. 32A-32E are illustrations showing a targeting guide 500C according to another embodiment. The targeting guide 500C is a variation on the targeting guide structures 500, 500A, and 500B. The targeting guide 500C comprises a handle portion 505 and a guide portion 520. At the distal end of the guide portion 520 is provided at least one guide hole 521 similar to the targeting guide 500, 500A, and 500B. Although the illustrated example only shows one guide hole 521, the guide portion 520 can be configured to have more than one guide holes as appropriate. The handle portion 505 comprises a translator part 510. The targeting guide 500C is configured to be used in the similar manner as the targeting guide embodiment 500 described above. The translator part 510 is intended to be inserted into the intramedullary canal of the cut end of the first bone portion B1 (the metatarsal shaft fragment) and used as a fulcrum to push and translate the second bone portion B2 (the metatarsal head fragment) in a lateral direction. Then, the guide hole 521 provided at the distal end of the guide portion 520 which extends in-line with the translator part 510 is in position to guide a guiding element G1 along a trajectory that is the trajectory intended for a bone screw to for fixating the two bone portions B1, B2.

However, in the targeting guide 500C, the handle portion 505 has a modular structure. The translator part 510 is provided on a detachable handle piece 505A. Referring to FIG. 31C, the detachable handle piece 505A is configured to be attached to and detached from the handle portion 505 by sliding into and out of a channel 505C provided on the handle portion 505. The detachable handle piece 505A comprises a pair of grooves 505G, one on each side along a portion of the length of the detachable handle piece 505A. The detachable handle piece 505A also comprises a set of teeth 505T (see FIG. 31B) provided along a portion of its length. The handle portion 505 is provided with a detent mechanism 505D that cooperates with the set of teeth 505T when the detachable handle piece 505A slides into the handle portion 505. The detent mechanism 505D allows the position of the detachable handle piece 505A in the handle portion 505 to be selectively adjusted in an incremental manner. The increment being determined by the size and spacing of the teeth 505T. This modular configuration of the handle portion 505 allows more adjustability for positioning the guide wire for the bone screw for fixating the two bone portions B1, B2.

According to an aspect of the present disclosure, a system or a kit for assisting with targeting of drilling bones is disclosed. The kit can comprise one or more of the targeting guides 100, 100A, 100B, 100C, 100D, 200A, 200B, 200C, 200D, 200E, 200F, 300, 300A, 300B, 300C, 400, 500, 500A, 500B, and 500C described herein and one or more of guide wires W, and guide sleeves SL, for the guide wires. The kit can also include screws, burr for making the osteotomy, periosteal elevators, scalpel, etc.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

We claim:

1. A targeting guide comprising:

a first portion comprises an elongated shape defining a first end and a second end;

an anchor guide pivotally attached to the first end of the first portion, wherein the anchor guide pivots with respect to the first end of the first portion about a hinge axis, wherein the anchor guide is configured to be affixed to one portion of a bone by an anchoring element;

wherein the anchoring element extends along a first axis;

wherein the first axis defines an alignment plane that is orthogonal to the hinge axis; and a second portion pivotally attached to the second end of the first portion;

wherein the second portion pivots about a pivot axis;

wherein the second portion comprises at least one guide hole, wherein the at least one guide hole extends through the second portion such that its longitudinal axis defines a second axis;

wherein the second axis is parallel to the alignment plane throughout the pivoting motion of the second portion;

wherein the second portion is pivotally attached to the first portion via a pivot pin;

wherein the first portion comprises at least one slot that extends along a portion of the first portion and the pivot pin extends through the at least one slot.

2. The targeting guide of claim 1, wherein the anchor guide comprises a channel sized and configured to receive the anchoring element therethrough for affixing the anchor guide to the one portion of the bone and the channel extends through the anchor guide on the first axis.

3. The targeting guide of claim 2, wherein the anchor guide comprises an anchoring element for affixing the anchor guide to the one portion of the bone, wherein the anchoring element is integral to the anchor guide.

4. The targeting guide of claim 1, wherein the second axis lies in the alignment plane.

5. The targeting guide of claim 1, wherein the second axis lies at a distance away from the alignment plane.

6. The targeting guide of claim 1, wherein a longitudinal axis of the first portion of the targeting guide is defined extending from the first end to the second end of the first portion and the longitudinal axis intersects the hinge axis and the pivot axis.

7. The targeting guide of claim 1, wherein the second portion comprises two or more guide holes and are all located on one side of the pivot axis.

8. A kit comprising:

at least one guide wire;

a targeting guide comprising:

a first portion comprises an elongated shape defining a first end and a second end;

an anchor guide pivotally attached to the first end of the first portion, wherein the anchor guide pivots with respect to the first end of the first portion about a hinge axis, wherein the anchor guide is configured to be affixed to one portion of a bone by an anchoring element;

wherein the anchoring element extends along a first axis;

wherein the first axis defines an alignment plane that is orthogonal to the hinge axis; and a second portion pivotally attached to the second end of the first portion;

wherein the second portion pivots about a pivot axis;

wherein the second portion comprises at least one guide hole, wherein the at least one guide hole extends through the second portion such that its longitudinal axis defines a second axis;

wherein the second axis is parallel to the alignment plane throughout the pivoting motion of the second portion;

wherein the second portion is pivotally attached to the first portion via a pivot pin;

wherein the first portion comprises at least one slot that extends along a portion of the first portion and the pivot pin extends through the at least one slot.

9. The kit of claim 8, wherein the anchor guide comprises a channel sized and configured to receive the anchoring element therethrough for affixing the anchor guide to the one portion of the bone and the channel extends through the anchor guide on the first axis.

10. The kit of claim 9, wherein the anchor guide comprises an anchoring element for affixing the anchor guide to the one portion of the bone, wherein the anchoring element is integral to the anchor guide.

11. The kit of claim 8, wherein the second axis lies in the alignment plane.

12. The kit of claim 8, wherein the second axis lies at a distance away from the alignment plane.

13. The kit of claim 8, wherein a longitudinal axis of the first portion of the targeting guide is defined extending from the first end to the second end of the first portion and the longitudinal axis intersects the hinge axis and the pivot axis.

14. The kit of claim 8, wherein the second portion comprises two or more guide holes and are all located on one side of the pivot axis.

* * * * *